(12) United States Patent
Guzman

(10) Patent No.: US 9,814,857 B2
(45) Date of Patent: Nov. 14, 2017

(54) METHOD AND CORRESPONDING KIT FOR ADMINISTERING AN ADDUCTOR CANAL BLOCK

(71) Applicant: Avent, Inc., Alpharetta, GA (US)

(72) Inventor: Michael F. Guzman, Fortville, IN (US)

(73) Assignee: Avent, Inc., Alpharetta, GA (US)

( * ) Notice: Subject to any disclaimer, the term of this patent is extended or adjusted under 35 U.S.C. 154(b) by 13 days.

(21) Appl. No.: 15/002,481

(22) Filed: Jan. 21, 2016

(65) Prior Publication Data

US 2016/0136382 A1     May 19, 2016

Related U.S. Application Data

(62) Division of application No. 13/359,445, filed on Jan. 26, 2012, now Pat. No. 9,265,897.

(Continued)

(51) Int. Cl.
*A61M 19/00* (2006.01)
*A61B 46/00* (2016.01)
(Continued)

(52) U.S. Cl.
CPC .......... *A61M 19/00* (2013.01); *A61B 1/3132* (2013.01); *A61B 17/3403* (2013.01); *A61B 46/00* (2016.02); *A61B 46/20* (2016.02); *A61M 5/142* (2013.01); *A61M 5/158* (2013.01); *A61M 5/1723* (2013.01); *A61M 5/42* (2013.01); *A61M 5/427* (2013.01); *A61M 5/46* (2013.01); *A61M 25/06* (2013.01); *A61M 25/065* (2013.01); *A61M 25/0662* (2013.01); *A61M 25/0668* (2013.01); *A61B 5/1106* (2013.01); *A61B 5/4821* (2013.01); *A61B 8/0841* (2013.01); *A61B 17/3401* (2013.01);
(Continued)

(58) Field of Classification Search
CPC ... A61B 17/3403; A61B 1/3132; A61B 46/00; A61B 46/20; A61B 8/0841; A61M 19/00; A61M 2005/1726; A61M 2025/0007; A61M 2025/0681; A61M 2210/1003; A61M 2210/1017; A61M 2210/1021; A61M 25/06
See application file for complete search history.

(56) References Cited

U.S. PATENT DOCUMENTS

| 5,562,695 | A | 10/1996 | Obenchain |
| 5,730,754 | A | 3/1998 | Obenchain |

(Continued)

OTHER PUBLICATIONS

Buckenmaier et al. Military Advanced Regional Anesthesia & Analgesia Handbook. 2008.*

(Continued)

*Primary Examiner* — Amanda Lauritzen Moher
(74) *Attorney, Agent, or Firm* — Dority & Manning, P.A.

(57) ABSTRACT

Apparatus for administering certain nerve blocks includes a sheath constructed from a flexible ultrasound echogenic material, a more rigid introducer/dilator for introducing the sheath into the patient, and an ultrasound echogenic catheter for inserting through the sheath once the distal end of the sheath is in place adjacent the nerve(s) to be blocked and the introducer/dilator has been withdrawn. The catheter has provisions at its proximal end for connecting to a source of local anesthetic. Methods for use of this apparatus are also described.

4 Claims, 39 Drawing Sheets

Related U.S. Application Data

(60) Provisional application No. 61/436,260, filed on Jan. 26, 2011, provisional application No. 61/472,264, filed on Apr. 6, 2011, provisional application No. 61/478,640, filed on Apr. 25, 2011, provisional application No. 61/506,391, filed on Jul. 11, 2011.

(51) Int. Cl.
    *A61M 5/42*     (2006.01)
    *A61M 25/06*     (2006.01)
    *A61B 1/313*     (2006.01)
    *A61M 5/142*     (2006.01)
    *A61B 46/20*     (2016.01)
    *A61M 5/46*     (2006.01)
    *A61M 5/158*     (2006.01)
    *A61M 5/172*     (2006.01)
    *A61M 25/00*     (2006.01)
    *A61B 17/34*     (2006.01)
    *A61B 5/11*     (2006.01)
    *A61B 5/00*     (2006.01)
    *A61B 8/08*     (2006.01)
    *A61M 29/00*     (2006.01)

(52) U.S. Cl.
    CPC ..... *A61M 29/00* (2013.01); *A61M 2005/1726* (2013.01); *A61M 2025/0007* (2013.01); *A61M 2025/0681* (2013.01); *A61M 2210/1003* (2013.01); *A61M 2210/1017* (2013.01); *A61M 2210/1021* (2013.01); *Y10S 514/818* (2013.01)

(56) References Cited

U.S. PATENT DOCUMENTS

| | | |
|---|---|---|
| 5,853,373 A | 12/1998 | Griffith et al. |
| 5,916,172 A | 6/1999 | Hodges et al. |
| 6,101,412 A | 8/2000 | Duhaylongsod |
| 6,185,451 B1 | 2/2001 | Richardson et al. |
| 6,347,247 B1 | 2/2002 | Dev et al. |
| 6,491,647 B1 | 12/2002 | Bridger et al. |
| 6,496,561 B1 | 12/2002 | Meyer et al. |
| 6,716,412 B2 | 4/2004 | Unger |
| 6,832,984 B2 | 12/2004 | Stelzer et al. |
| 6,865,416 B2 | 3/2005 | Dev et al. |
| 6,994,700 B2 | 2/2006 | Elkins et al. |
| 7,104,981 B2 | 9/2006 | Elkins et al. |
| 7,149,574 B2 | 12/2006 | Yun et al. |
| 7,239,912 B2 | 7/2007 | Dobak, III |
| 7,493,154 B2 | 2/2009 | Bonner et al. |
| 8,882,673 B2 | 11/2014 | Guzman |
| 9,265,897 B2 | 2/2016 | Guzman |
| 2002/0103494 A1 | 8/2002 | Pacey |
| 2002/0177887 A1 | 11/2002 | Krebs |
| 2004/0015133 A1 | 1/2004 | Karim |
| 2004/0049231 A1* | 3/2004 | Hafer ................ A61B 17/3401 607/3 |
| 2004/0087877 A1 | 5/2004 | Besz et al. |
| 2005/0027262 A1* | 2/2005 | Appling ................ A61M 39/22 604/246 |
| 2005/0107829 A1 | 5/2005 | Edwards et al. |
| 2005/0171575 A1 | 8/2005 | Dev et al. |
| 2006/0015131 A1 | 1/2006 | Kierce et al. |
| 2006/0025797 A1 | 2/2006 | Lock et al. |
| 2006/0089633 A1 | 4/2006 | Bleich et al. |
| 2006/0095059 A1 | 5/2006 | Bleich et al. |
| 2006/0161998 A1* | 7/2006 | Romans ................ A01K 67/027 800/9 |
| 2006/0206155 A1 | 9/2006 | Ben-David et al. |
| 2007/0021686 A1 | 1/2007 | Gellman et al. |
| 2007/0060954 A1 | 3/2007 | Cameron et al. |
| 2007/0156179 A1 | 7/2007 | S.E. |
| 2007/0219596 A1 | 9/2007 | Dobak, III |
| 2007/0225768 A1 | 9/2007 | Dobak, III |
| 2008/0132926 A1 | 6/2008 | Eichmann et al. |
| 2008/0275458 A1 | 11/2008 | Bleich et al. |
| 2009/0005774 A1 | 1/2009 | Fernald |
| 2009/0048537 A1 | 2/2009 | Lyndon et al. |
| 2010/0210997 A1 | 8/2010 | Gharib |
| 2012/0059308 A1 | 3/2012 | Hsu et al. |
| 2014/0316268 A1 | 10/2014 | Kafiluddi et al. |
| 2014/0343406 A1 | 11/2014 | Damjanovic |
| 2014/0350576 A1 | 11/2014 | Patel et al. |
| 2015/0059768 A1 | 3/2015 | Guzman |
| 2015/0306350 A1 | 10/2015 | Hofius et al. |
| 2016/0136381 A1 | 5/2016 | Guzman |
| 2016/0158483 A1 | 6/2016 | Guzman |

OTHER PUBLICATIONS

Karmakar et al. A Practice of Anesthesia for Infants and Children (Fourth Edition): Chapter 43—Ultrasound-Guided Regional Anesthesia: pp. 911-938: Manoj K. Karmakar, Wing H. Kwok. Available online Nov. 11, 2009.*
Transversus Abdominis Plane (TAP) Block, New York School of Regional Anesthesia, 2009, vol. 12.
Ultrasound-guided Subcostal Transversus Abdominis Plane Block, International Journal of Ultrasound and Applied Technologies in Periperative Care, Jan.-Apr. 2010.
Redefining Recovery, The On-Q Tunneling System—Taking Effective Pain Relief a Step Beyond.
Ultrasound-Guided Transversus Abdominis Plane Catheters and Ambulatory Perineural Infusions for Infusions for Outpatient Inguinal Hernia Repair, Reg. Anesth. Pain Med., Nov. 2010.
Transversus Abdominis Plane (TAP) Block, Ultrasound for Regional Anesthesia, 2008.
Product Description, On-Q Catheters & Introducers, I-Flow Corporation.
Product Description, Contiplex and Stimuplex, B. Braun Melsungen, Germany.
Product Description, On-Q Post-Op Pain Relief System, I-Flow Corporation.
Article, Tighe, et al., Paravertebral block, Continuing Education in Anesthesia, Critical Care & Pain, 2010, vol. 10, Issue 5, pp. 133-137.
Handbook, Buckenmaier, III, et al., Military Advanced Regional Anesthesia and Analgesia, 2008, Chapter 12, pp. 45-48.
Barrington et al., "Spread of Injectate after Ultrasound-Guide Subcostal Transversus Abdominis Plane Block: A Cadaveric Study", Anesthesia 2009, 64, pp. 745-750.
Batra et al., "Paravertebral Block", Journal of Anesthesiology Clinical Pharmacology, Jan.-Mar. 2011, 27(1): 5-11.
Belavy et al., "Ultrasound-Guided Transversus Abdominis Plane Block for Analgesia after Caesarean Delivery", British Journal of Anesthesia, 2009, 103(5): 726-3.
Mukhtar, "Transversus Abdominis Plane (TAP) Block", The Journal of New York School of Regional Anesthesia, 2006.
Mukhtar, "Ultrasound-Guided Transversus Abdominis Plane Block", Correspondence, British Journal of Anesthesia.
Niraj et al., "Analgesic Efficacy of Ultrasound-Guided Transversus Abdominis Plane Block in Patients Undergoing Open Appendicectomy", British Journal of Anesthesia, 2009, 103(4): 601-5.
O'Connor, "Subcostal Transversus Abdominis Plane Block", Anesthesia, 2010, 65, pp. 82-93.
Tran et al., "Determination of Spread of Injectate after Ultrasound-Guided Transversus Abdominis Plane Block: A Cadaveric Study", British Journal of Anesthesia, 2009, 102(1): 123-7.
Arregui et al., Laparoscopic Mesh Repair of Inguinal Hernia Using a Preperitoneal Approach: A Preliminary Report, Surgical Laparoscopy & Endoscopy, 2(1), pp. 53-58, 1992.
El-Dawlatly et al., Ultrasound-guided transversus abdominis plane block: description of a new technique and comparison with conventional systemic analgesia during laparoscopic cholecystectomy, British Journal of Anesthesia, 102 (6), 763-7, 2009, 5 pages.

(56) References Cited

OTHER PUBLICATIONS

Hebbard et al., Transversailis fascia plane block, a novel ultrasound-guided abdominal wall nerve block, Can J. Anesth/J Can Anesth, vol. 56, pp. 618-620, 2009.

Hebbard et al., Subcostal Transversus Abdominis Plane Block Under Ultrasound Guidance, Anesthesia & Analgesia, 106(2), pp. 674-675, 2008.

Jankovic, et al., Transversus abdominis plane block: The Holy Grail of anaesthisia for (lower) abdominal surgery, Periodicum Bilogorum, 111(2), pp. 203-208, 2009.

Niraj et al., Oblique sub-costal transversus abdominis plane (TAP) catheters: an alternative to epidural analgesia after upper abdominal surgery, Journal of the Association of Anaesthetists of Britain and Ireland, vol. 64, pp. 1137-1140, 2009.

Pranevicius et al., Using Two Needles for Multiple Injection Nerve Blocks Avoids Manipulation After Local Anesthetic Injection, Anesthesia and Analgesia, 104(5), p. 1308, 2007.

Walter et al., Ultrasound imaging for transversus abdominis blocks, Anaesthesia, vol. 63, p. 211, 2008.

\* cited by examiner

METHOD AND CORRESPONDING KIT FOR ADMINISTERING AN ADDUCTOR CANAL BLOCK

RELATED APPLICATIONS

This application is a divisional of U.S. patent application Ser. No. 13/359,445, filed on Jan. 26, 2012, which claims benefit under 35 U.S.C. §119(e) to: U.S. Ser. No. 61/436,260, filed Jan. 26, 2011; U.S. Ser. No. 61/472,264 filed Apr. 6, 2011; U.S. Ser. No. 61/478,640 filed Apr. 25, 2011; and, U.S. Ser. No. 61/506,391 filed Jul. 11, 2011. The disclosures of: U.S. Ser. No. 61/436,260; U.S. Ser. No. 61/472,264; U.S. Ser. No. 61/478,640; and, U.S. Ser. No. 61/506,391 are hereby incorporated herein by reference.

The invention relates to methods and apparatus for administering percutaneous nerve blocks including, for example: laparoscopic transversus abdominis plane (hereinafter sometimes LAP TAP) blocks; open TAP blocks; fascia iliaca blocks (hereinafter sometimes FIBs); paravertebral blocks; femoral nerve blocks; brachial plexus nerve blocks; sciatic nerve blocks; saphenous nerve blocks; and the like.

According to an aspect, a method for administering a transversus abdominis plane (TAP) block to a patient comprises: distending the patient's abdomen; while the patient's abdomen is distended, penetrating the exterior wall of the abdomen with a needle sheathed within a sheath having an open distal end through which a distal end of the needle projects; advancing the sheathed needle to the belly of the transversus abdominis rectus muscle (TAR); administering an amount of a local anesthetic; viewing the peritoneum for a bulge adjacent the location where the local anesthetic is being administered; removing the needle from the sheath; inserting a catheter through the sheath until the catheter extends from a distal end of the sheath; removing the sheath; connecting a proximal end of the catheter to a source of local anesthetic; and, commencing anesthesia.

Illustratively according to this aspect, viewing the peritoneum for a bulge adjacent the location where the local anesthetic is being administered comprises viewing the peritoneum using (a) laparoscopic camera(s) and monitor(s).

Illustratively according to this aspect, advancing the sheathed needle to the belly of the TAR comprises penetrating the patient's skin, fat, external oblique muscle, internal oblique muscle, and TAR, and sliding the sheathed needle in a plane parallel to and just outside the patient's peritoneum.

Illustratively according to this aspect, connecting a proximal end of the catheter to a source of local anesthetic comprises attaching an adapter to an external end of the catheter and attaching the adapter to an infusion pump.

According to another aspect, a method for administering a paravertebral block (PVB) to a patient comprises: marking at least some of the patient's cervical (C) and thoracic (T) spinous processes; determining the depth of the patient's transverse process and external intercostal muscle at each C and/or T level to be blocked; administering local anesthetic at the T5 level; introducing a first needle sheathed within a first sheath having an open distal end through which a distal end of the first needle projects at the T5 level, approximately 1.25-2.54 cm lateral from the patient's T5 spinous process under the skin to a depth just above the patient's external intercostal muscle; advancing the sheathed first needle cephalad, at a depth just above the external intercostal muscle of each vertebra, maintaining substantially constant lateral distance of approximately 1.25-2.54 cm from the patient's spinous process; halting advancement of the sheathed first needle when the highest level marked C spinous process is reached; withdrawing the first needle from the first sheath; advancing a first catheter into the first sheath; removing the first sheath while leaving the first catheter in place; connecting a proximal end of the first catheter to a source of local anesthetic; and, commencing anesthesia.

Illustratively according to this aspect, the method is administered to the patient with the patient in the prone position.

Illustratively according to this aspect, the method is administered to the patient with the patient in the lateral decubitus position.

Illustratively according to this aspect, marking at least some of the patient's cervical (C) and thoracic (T) spinous processes comprises marking the patient's C7 to T5 spinous processes.

Illustratively according to this aspect, advancing the sheathed first needle cephalad is performed under ultrasound guidance.

Illustratively according to this aspect, advancing the sheathed first needle cephalad is aided with intermittent injection of local anesthetic.

Illustratively according to this aspect, connecting a proximal end of the first catheter to a source of local anesthetic comprises attaching an adapter to an external end of the first catheter and attaching the adapter to an infusion pump.

Further illustratively according to this aspect, the method comprises: introducing a second needle sheathed within a second sheath having an open distal end through which a distal end of the second needle projects at the T5 level, approximately 1.25-2.54 cm lateral from the patient's T5 spinous process under the skin to a depth just above the patient's external intercostal muscle; advancing the sheathed second needle caudad, at a depth just above the external intercostal muscle of each vertebra, maintaining substantially constant lateral distance from the patient's spinous process of approximately 1.25-2.54 cm; halting advancement of the sheathed second needle when the lowest level marked T spinous process is reached; withdrawing the second needle from the second sheath; advancing a second catheter into the second sheath; removing the second sheath while leaving the second catheter in place; connecting a proximal end of the second catheter to a source of local anesthetic; and, commencing anesthesia.

Further illustratively according to this aspect, the method comprises: introducing a second needle sheathed within a second sheath having an open distal end through which a distal end of the second needle projects at the T5 level on the opposite lateral side of the patient's spine from the first sheathed needle, approximately 1.25-2.54 cm lateral from the patient's T5 spinous process under the skin to a depth just above the patient's external intercostal muscle; advancing the sheathed second needle cephalad, at a depth just above the external intercostal muscle of each vertebra, maintaining substantially constant lateral distance from the patient's spinous process of approximately 1.25-2.54 cm; halting advancement of the sheathed second needle when the highest level marked C spinous process is reached; withdrawing the second needle from the second sheath; advancing a second catheter into the second sheath; removing the second sheath while leaving the second catheter in place; connecting a proximal end of the second catheter to a source of local anesthetic; and, commencing anesthesia.

According to another aspect, a method for administering an adductor canal block (ACB) to a patient comprises: identifying the patient's sartorius muscle; advancing a needle sheathed within a sheath having an open distal end through which a distal end of the needle projects to the base of the sartorius muscle; injecting a few milliters of a local anesthetic to identify the bottom of the sartorius fascia; advancing the sheathed needle through the sartorius fascia; administering an additional approximately 30 milliters of a local anesthetic; removing the needle, leaving the sheath in the patient's adductor canal; inserting a catheter into the sheath and advancing a distal end of the catheter through the sheath to the adductor canal; removing the sheath; connecting a proximal end of the catheter to a source of local anesthetic; and, commencing anesthesia.

Illustratively according to this aspect, identifying the patient's sartorius muscle comprises identifying the patient's sartorius muscle using ultrasound.

Illustratively according to this aspect, connecting a proximal end of the catheter to a source of local anesthetic and commencing anesthesia comprise connecting a proximal end of the catheter to a constant infusion pump to deliver the local anesthetic postoperatively at an initial flow rate of about 6 ml/hour and at a rate of about 2-4 ml/hr per day one day postoperative.

According to another aspect, a method for administering a peripheral nerve block to a patient comprises: penetrating the body of the patient with a first needle sheathed within a first sheath having an open distal end through which a distal end of the first needle projects; the first needle being treated to render its surface electrically non-conductive except adjacent its distal end; advancing the sheathed first needle to the general location of the nerve to be blocked; passing a current through the first needle and the patient's body to stimulate nerves in the area of the distal end of the first needle; observing the effect of such stimulation; repeating until the distal end of the first needle is at the location of the peripheral nerve to be blocked; administering local anesthetic through the first needle; withdrawing the first needle; inserting a first catheter through the first sheath; connecting a proximal end of the first catheter to a source of local anesthetic; and, commencing anesthesia via the first catheter.

Further illustratively according to this aspect, the method comprises: introducing a second needle sheathed within a second sheath having an open distal end through which a distal end of the second needle projects into the body of the patient in a direction other than the direction in which the sheathed first needle was directed; advancing the sheathed second needle to the general location of the distal end of the first catheter; withdrawing the second needle; inserting a second catheter through the second sheath; advancing the second catheter past the distal end of the first sheath; removing the first sheath; removing the second sheath; connecting a proximal end of the second catheter to a source of local anesthetic; and, commencing anesthesia via the second catheter.

Further illustratively according to this aspect, the method comprises providing a stimulating clip adjacent a proximal end of the first needle for coupling the first needle to a peripheral nerve stimulator to facilitate passing a current through the first needle and the patient's body to stimulate nerves in the area of the distal end of the first needle.

According to another aspect, a method for administering a peripheral nerve block to a patient comprises: penetrating the body of the patient with a first needle sheathed within a first sheath having an open distal end through which a distal end of the first needle projects; advancing the sheathed first needle to the general location of the nerve to be blocked; administering local anesthetic through the first needle; withdrawing the first needle; inserting a first catheter through the first sheath; connecting a proximal end of the first catheter to a source of local anesthetic; commencing anesthesia via the first catheter; introducing a second needle sheathed within a second sheath having an open distal end through which a distal end of the second needle projects into the body of the patient in a direction other than the direction in which the sheathed first needle was directed; advancing the sheathed second needle to the general location of the distal end of the first catheter, withdrawing the second needle; inserting a second catheter through the second sheath; advancing the second catheter past the distal end of the first sheath; removing the first sheath; removing the second sheath; connecting a proximal end of the second catheter to a source of local anesthetic; and, commencing anesthesia via the second catheter.

According to another aspect, a kit for administering a transversus abdominis plane (TAP) block to a patient comprises a needle, a sheath having an open distal end through which a distal end of the needle can project, and a catheter of a size permitting the catheter to be advanced through the sheath until the catheter extends from a distal end of the sheath, the catheter having a proximal end permitting connecting a proximal end of the catheter to a source of local anesthetic.

Further illustratively according to this aspect, the kit comprises an adapter for coupling an external end of the catheter to an infusion pump.

Further illustratively according to this aspect, the kit comprises a surgical drape having an opening through which a procedure may be performed using the kit.

Further illustratively according to this aspect, the kit comprises an amount of a local anesthetic.

According to another aspect, a kit for administering a paravertebral block (PVB) to a patient comprises a first needle, a first sheath having an open distal end through which a distal end of the first needle can project, and a first catheter of a size permitting the first catheter to be advanced through the first sheath until the first catheter extends from a distal end of the first sheath, the first catheter having a proximal end permitting connecting a proximal end of the first catheter to a source of local anesthetic.

Further illustratively according to this aspect, the kit comprises a marker for marking the skin of a patient.

Further illustratively according to this aspect, the kit comprises an amount of a local anesthetic.

Further illustratively according to this aspect, the kit comprises a surgical drape having an opening through which a procedure may be performed using the kit.

Further illustratively according to this aspect, the kit comprises an adapter for coupling an external end of the catheter to an infusion pump.

Further illustratively according to this aspect, the kit comprises a second needle, a second sheath having an open distal end through which a distal end of the second needle can project, a second catheter of a size permitting the second catheter to be advanced through the second sheath until the second catheter extends from a distal end of the second sheath, the second catheter having a proximal end permitting connecting a proximal end of the second catheter to a source of local anesthetic.

According to another aspect, a kit for administering an adductor canal block (ACB) to a patient comprises a needle, a sheath having an open distal end through which a distal end of the needle can project, and a catheter of a size permitting the catheter to be advanced through the sheath until the catheter extends from a distal end of the sheath, the catheter having a proximal end permitting connecting a proximal end of the catheter to a source of local anesthetic.

Further illustratively according to this aspect, the kit comprises an adapter for coupling an external end of the catheter to an infusion pump.

Further illustratively according to this aspect, the kit comprises a surgical drape having an opening through which a procedure may be performed using the kit.

Further illustratively according to this aspect, the kit comprises an amount of a local anesthetic.

According to another aspect, a kit for administering a peripheral nerve block to a patient comprises a first needle treated to render its surface electrically non-conductive except adjacent its distal end, a first sheath having an open distal end through which a distal end of the first needle can project, a first catheter of a size permitting the first catheter to be advanced through the first sheath until the first catheter extends from a distal end of the first sheath.

Further illustratively according to this aspect, the kit includes a second needle, a second sheath having an open distal end through which a distal end of the second needle can project, and a second catheter of a size permitting the second catheter to be advanced through the second sheath until the second catheter extends from a distal end of the second sheath.

Further illustratively according to this aspect, the kit comprises a stimulating clip adjacent a proximal end of the first needle for coupling the first needle to a peripheral nerve stimulator to facilitate passing a current through the first needle and the patient's body to stimulate nerves in the area of the distal end of the first needle.

Further illustratively according to this aspect, the kit comprises an adapter for coupling an external end of the first catheter to an infusion pump.

Further illustratively according to this aspect, the kit comprises an adapter for coupling an external end of the second catheter to an infusion pump.

Further illustratively according to this aspect, the kit comprises a surgical drape having an opening through which a procedure may be performed using the kit.

Further illustratively according to this aspect, the kit comprises an amount of a local anesthetic.

According to another aspect, a kit for administering a peripheral nerve block to a patient comprises a first needle, a first sheath having an open distal end through which a distal end of the first needle can project, a first catheter of a size permitting the first catheter to be advanced through the first sheath until the first catheter extends from a distal end of the first sheath, a second needle, a second sheath having an open distal end through which a distal end of the second needle can project, and a second catheter of a size permitting the second catheter to be advanced through the second sheath until the second catheter extends from a distal end of the second sheath.

Further illustratively according to this aspect, the kit comprises an adapter for coupling an external end of the first catheter to an infusion pump.

Further illustratively according to this aspect, the kit comprises an adapter for coupling an external end of the second catheter to an infusion pump.

Further illustratively according to this aspect, the kit comprises a surgical drape having an opening through which a procedure may be performed using the kit.

Further illustratively according to this aspect, the kit comprises an amount of a local anesthetic.

According to another aspect, a kit for administering a peripheral nerve block to a patient comprises an ultrasound opaque or semi-opaque introducer and an ultrasound opaque or semi-opaque catheter of a size permitting the catheter to be advanced through the introducer until the catheter extends from a distal end of the introducer.

According to another aspect, a method for administering a peripheral nerve block to a patient comprises providing an ultrasound opaque or semi-opaque introducer and providing an ultrasound opaque or semi-opaque catheter of a size permitting the catheter to be advanced through the introducer until the catheter extends from a distal end of the introducer, and advancing the catheter through the introducer until the catheter extends from a distal end of the introducer.

Illustratively according to this aspect, advancing the catheter through the introducer until the catheter extends from a distal end of the introducer is performed under ultrasound guidance.

The invention may be understood by referring to the following detailed descriptions and accompanying drawings. In the drawings:

FIG. 18 illustrates a partly cut away longitudinal sectional side elevational diagram of apparatus constructed according to the invention;

FIGS. 28-39 illustrate various phases in the progress of a supraclavicular block.

Figure 1:
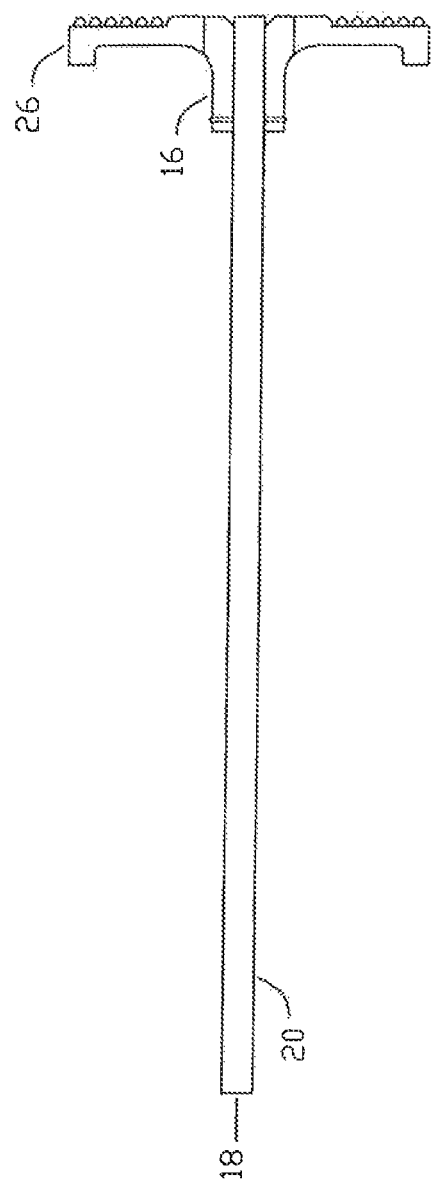
FIG. 1 illustrates a 3½ inch (about 8.9 cm.) needle/sheath (introducer/sheath) assembled.

The apparatus includes a sheath, an introducer/dilator, and a catheter which illustratively and desirably may have echogenic properties.

The sheath could be similar to I-flow's soaker sheath (I-Flow soaker kit, ref PM030, part 5001731) with its inherent echogenic properties, or using material similar to I-Flow soaker sheath echogenic material in a sheath construction similar to a Covidien Versaport™ bladeless low profile trocar, ref NB3SHFLP, 2 mm short. If the Covidien trocar-type sheath is used, the sheath needs to be a smaller diameter than the Covidien Versaport™ 2 mm short.

The introducer 30 could be an epidural needle similar to B. Braun (17 gauge 4½ inch Tuohy needle, product code E11745T, ref 332181) or Becton, Dickinson Weiss needle (ref 405190, 18 gauge, 5 inch), and could be insulated to permit stimulating nerve blocks or non-insulated for ultrasound guided nerve blocks. Another option for the introducer 30 would be a Veress needle such as Ethicon's pneumoneedle (150 mm ref PN150). The Veress needle option provides a smoother transition than a typical Tuohy epidural needle's distal end. The sheath can be tapered much more closely to a Veress needle and avoid distal sheath shearing than a Tuohy needle when penetrating a patient's skin. Another option for the introducer 30 would be similar to the obturator from a Covidien bladeless low profile trocar (refNB3SHFLP). This Covidien option would provide a smooth, continuous, distal end with less penetrating qualities and be similar to many non-cutting introducer-trocars.

The apparatus 10 includes a sheath 12 having an open proximal end 16 and an open distal end 18. The sheath 12 is constructed from a flexible ultrasound echogenic material to permit location of sheath 12 in a patient's body 14 by ultrasound. The sidewall 20 of the sheath 12 adjacent the open distal end 18 illustratively tapers 22 toward the distal end 18 to aid the insertion into the patient 14. This sheath 12 may be constructed with a side extension 26 near the proximal end 16. Such a side extension 26 may be useful to remove the sheath 12 from the introducer/dilator 30 into the patient 14, as will be explained.

The apparatus 10 also includes a more rigid introducer/dilator 30 for introducing the sheath 12 into the patient 14. The introducer/dilator 30 is sized to be inserted into the sheath 12 to rigidify the sheath 12 for insertion. The introducer/dilator 30 may include a tapered, for example, somewhat conical, tip 32 at its distal end 34. The base of the tip 32 is sized and shaped to provide with the taper 22 of sheath 12 a fairly continuous, smooth surface to aid in insertion of the sheath 12/introducer/dilator 30 assembly. Adjacent the point of the tip 32, passageways 36 may be provided through the introducer/dilator 30 for the introduction of fluid, again, typically liquid, species through the introducer/dilator 30 into the patient 14. A sealable or one way port may be provided at the proximal end 40 of the introducer/dilator 30 for introduction of such fluid species through a tube 41 and port 38 into the passageway 42 between ends 34, 40 through the port 38, down the length of the passageway 42 and out through the passageways 36 in the tip 32 into the body 14. Again, the introducer/dilator 30, particularly its tip 32, should be ultrasound echogenic to permit location of tip 32 in the body 14 by ultrasound.

The apparatus 10 further should have an ultrasound echogenic catheter, with characteristics and function similar to catheter 44. An example of an echogenic catheter includes a catheter 44 with a soaker tip 46 similar to the ON-Q® soaker catheter, part 4000950-1 (2.5 cm) available from I-Flow Corporation, for inserting through the sheath 12 once the apparatus has been properly placed by ultrasound or direct vision. If the sheath 12 is not a tearable type sheath, the catheter 44 does not have the ON-Q® soaker catheter's injection port, because the sheath 12 needs to be able to slide over the catheter 44 as the sheath 12 is removed from the patient's body 14. The end of the catheter 44 not in the body 14 then has a catheter adapter 48 snapped onto catheter part 50, to permit the catheter 44 to be connected to an infusion pump 52. The catheter adapter 48 would work similarly to the snaplock adapter available from Arrow Corporation, epidural kit, reference SJ-05501.

It is envisioned that sheaths 12 and introducer/dilators 30 will come in lengths for infants, children and small women, adults, and obese patients. It is envisioned that the needle lengths for non-stimulating kits will likely be one inch (about 2.5 cm.), two inches (about 5 cm.), three and one-half inches (about 8.9 cm.) and five inches (about 12.7 cm.). Kits with stimulating needles will have needles and sheaths in lengths of two inches (about 5 cm.) and three and one-half inches (about 8.9 cm.). The catheters will come in lengths necessary or desirable for the particular patient 14 and block with which they are to be used.

Typical procedures proceed as follows:

Percutaneous TAP Block

For both posterior and subcostal TAP blocks, the fascia under the patient 14's internal oblique muscle is identified by ultrasound in the appropriate anatomy for either a posterior or subcostal TAP block. The introducer/dilator 30 is inserted into the proximal end 16 of sheath 12 until tapered tip 32 projects from distal end 18 with the tip 32 and taper 22 forming a smooth contour. A small incision may need to be made through the patient 14's skin to permit the sheath 12/introducer/dilator 30 assembly to be pushed under ultrasound guidance to the plane between the internal oblique and the transversus muscles. Two distinct "pops" are felt by the operator during this process, the first when the tip 32 passes through the external oblique, and the second when the tip 32 passes through the internal oblique. The tip 32 is placed in the fascia directly under the internal oblique to permit administration of local anesthetic through tubing 41 and out of openings 36, and then extension of this pool of local anesthetic into an area in the transversus abdominis plane. The sheath 12/introducer/dilator 30 assembly is advanced slightly in the fluid area. The introducer/dilator 30 is then withdrawn from sheath 12. The catheter 44 is then introduced into sheath 12 and advanced an appropriate distance, as determined by the operator. The sheath 12 is then withdrawn, leaving the catheter 44 in place. A catheter adapter 48 is attached to the external end 50 of the catheter 44 and then connected to an infusion pump 52 such as the ON-Q® PainBuster® pump, filled with local anesthetic to permit the process to begin.

LAP TAP

Figure 11:
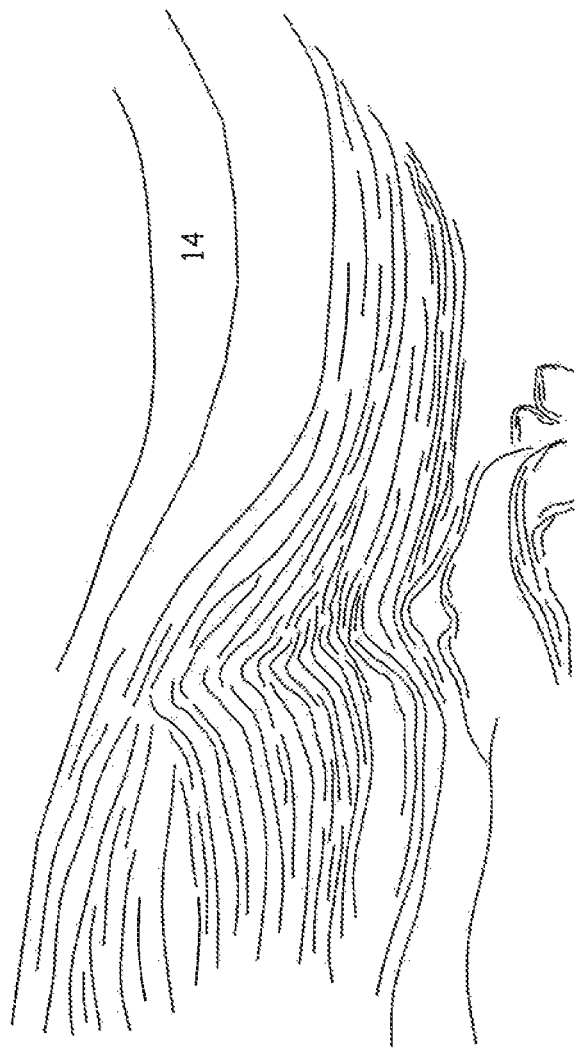
FIG. 11 illustrates the bulge in the peritoneum characteristic of successful administration of a laparascopic transversus abdominis plane block.

The surgeon performing a laparoscopic procedure can place a TAP block under direct vision at the end of an abdominal surgery. With the abdomen still distended with carbon dioxide, the surgeon can view the area inside the peritoneum using (a) standard laparoscopic camera(s) and monitor(s). Using the apparatus, the surgeon penetrates the patient 14's abdomen in the area of a typical posterior or subcostal TAP. The surgeon under direct camera vision penetrates through the skin, fat, external oblique, internal oblique, transversus abdominis, and slides the apparatus 10 in a plane parallel to and just above the patient 14's peritoneum. The distal end 18 of sheath 12 and tapered tip 32 are oriented in the belly of the transversus abdominis muscle. Local anesthetic is given through tubing 41. If the surgeon has the apparatus too deep, the surgeon will see the apparatus (with his/her laparoscopic camera), and upon injection of local anesthetic will notice the surface of the peritoneum is ballooning. The surgeon should then simultaneously withdraw the apparatus slowly out of the patient 14 and inject local anesthetic until a bulge is seen. See FIG. 11. This bulging indicates the transversus abdominis rectus muscle is separating from the internal oblique. External confirmation of the LAP TAP area may be checked with a sterile covered percutaneous ultrasound probe. The process then proceeds in a manner similar to the percutaneous TAP procedure described above. The introducer/dilator 30 is removed, the catheter 44 is advanced in the sheath 12, and the sheath 12 is removed leaving the catheter 44 in the belly of the transversus abdominis muscle. The adapter 48 is attached to the external and 50 of the catheter 44 and then connected to an infusion pump 52 to begin infusion.

Figure 12:
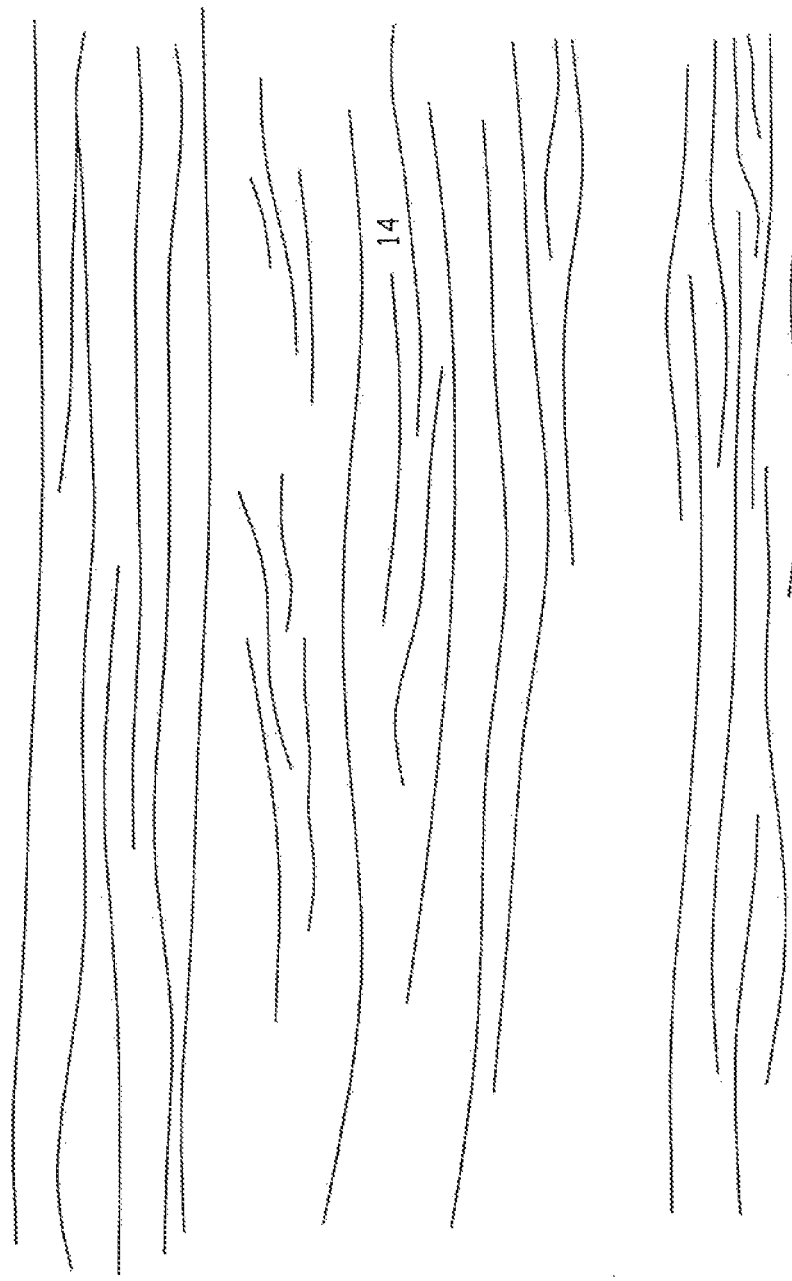
FIG. 12 illustrates an ultrasonogram of the abdomen of a patient who has received a laparascopic transversus abdominis plane block.

FIG. 12 illustrates an ultrasonogram of the abdomen of a patient who has received a laparascopic transversus abdominis plane block. The exterior oblique lies between the two lighter bands at the top of the ultrasonogram. The upper band is skin and fat. The second band is the fascia between the exterior oblique and interior oblique. The interior oblique lies between the second lighter band from the top and the second lighter band from the bottom. The second lighter band from the bottom is the fascia between the interior oblique and the transversus abdominis rectus. The transversus abdominis rectus lies between the second lighter band from the bottom and the bottom brighter band. The bottom brighter band is the peritoneum. A pool of local anesthetic is the dark area to the far right between the bottom two lighter bands.

Fascia Iliaca Block

The apparatus can also be used for placement of a continuous fascia iliaca block. The patient 14's appropriate area is located approximately two fingers lateral from the femoral nerve and two fingers below the inguinal crease. A small skin incision may be required. Then the sheath 12/introducer/dilator 30 assembly is manipulated to penetrate first the fascia lata and then the fascia iliaca. Local anesthetic is injected through tubing 41, distending the iliaca muscle, thereby providing a safe passage for advancing the sheath 12 off the introducer/dilator 30. The sheath 12 is now in an appropriate area to cause an anterior lumbar plexus block. The catheter 44 is advanced into the sheath 12 an appropriate distance, the sheath 12 is removed, leaving the catheter 44. The adapter 48 is attached to the external end 50 of the catheter 44 and then connected to an infusion pump 52 to begin infusion.

Figure 13:
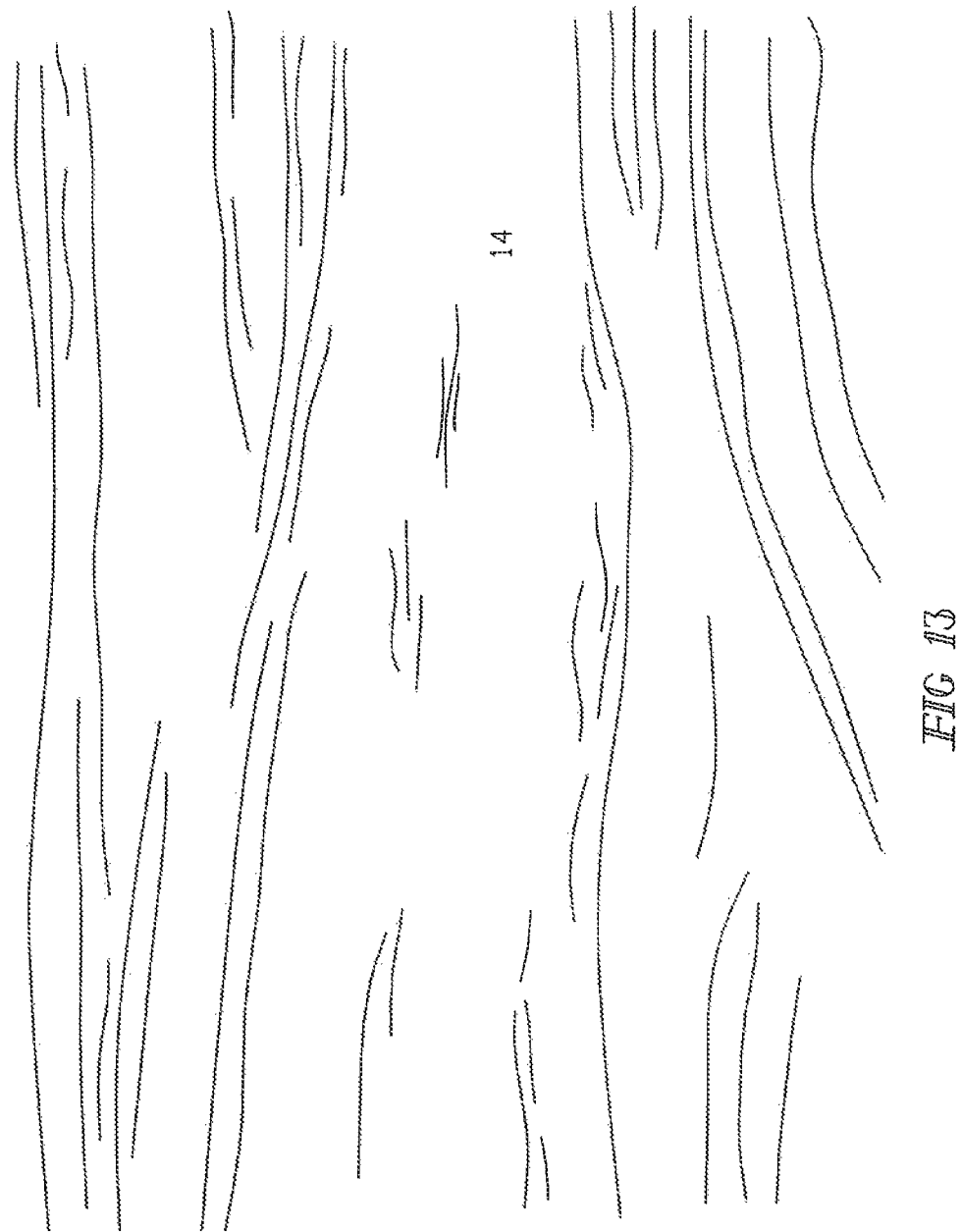
FIGS. 13-17 illustrate ultrasonograms of various phases in the progress of a fascia iliaca block.
Figure 14:
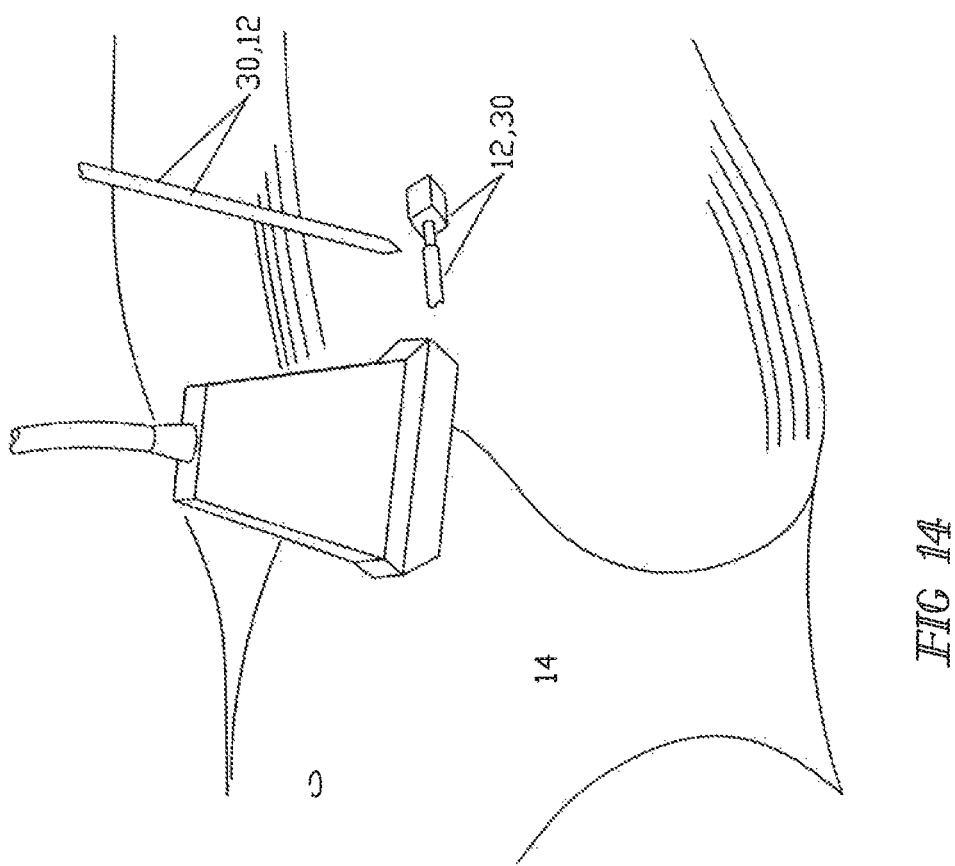
Figure 15:
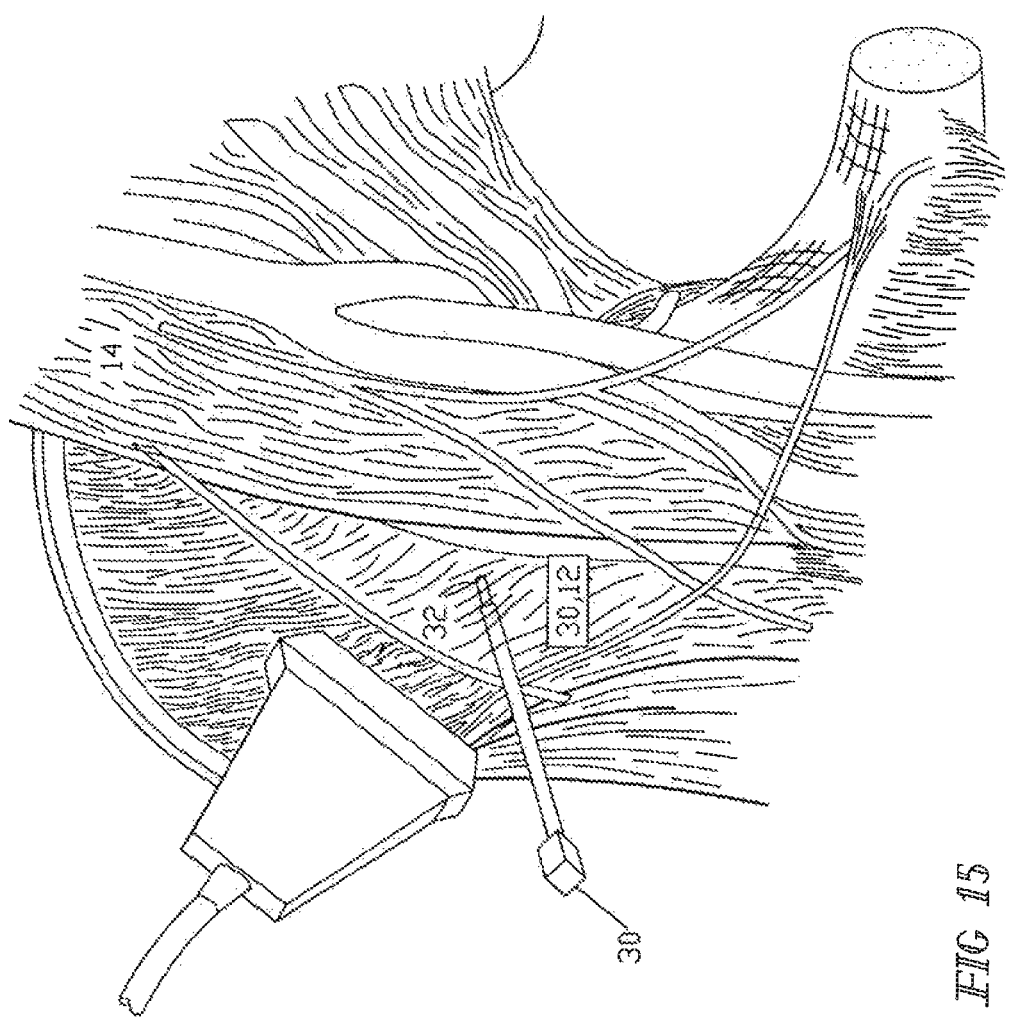
Figure 16:
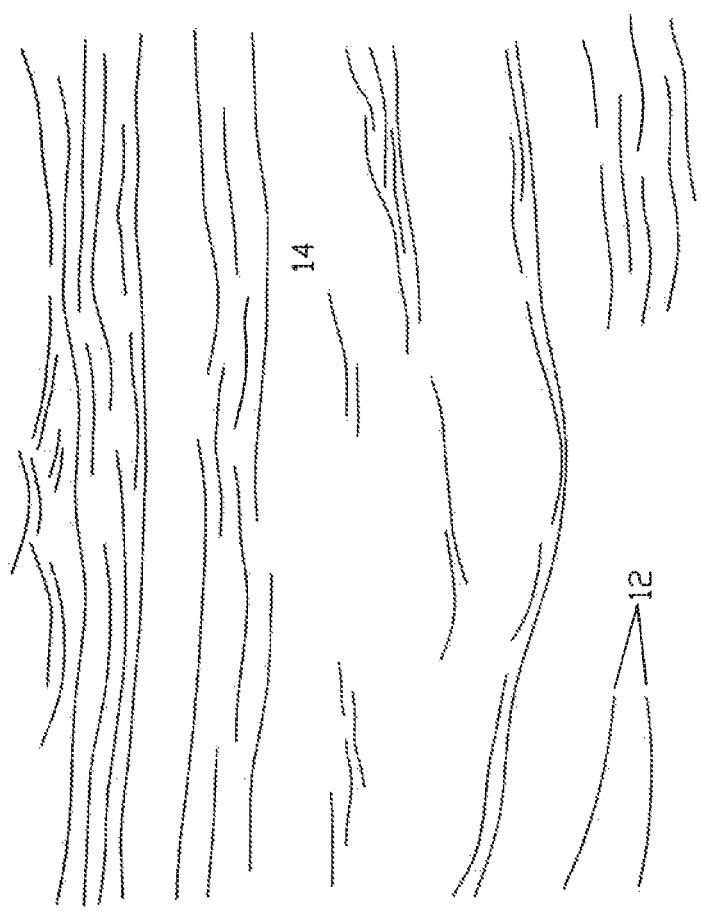
Figure 17:
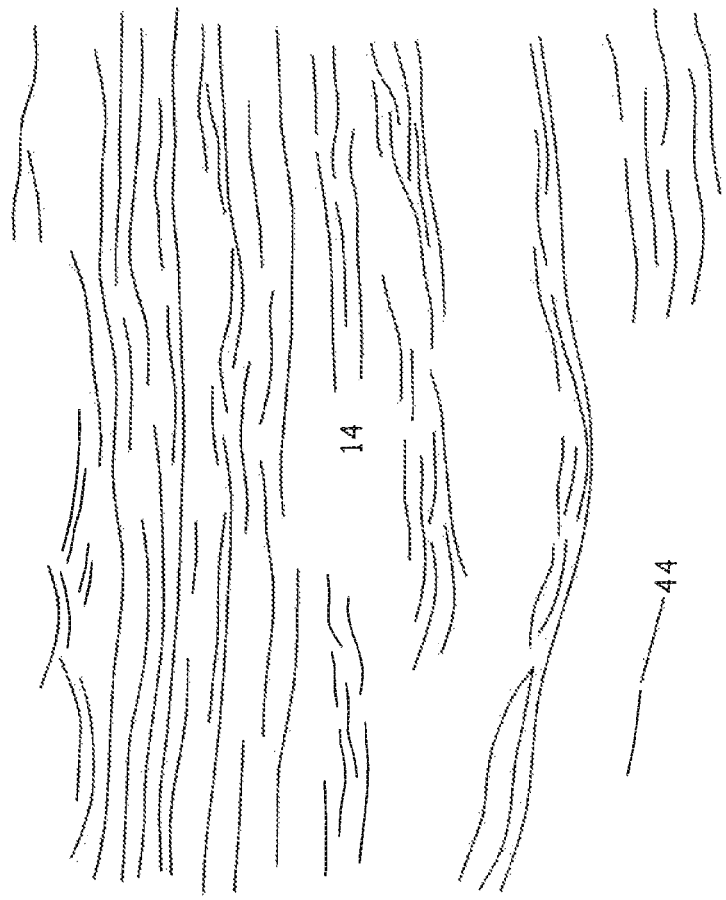
Figure 10:
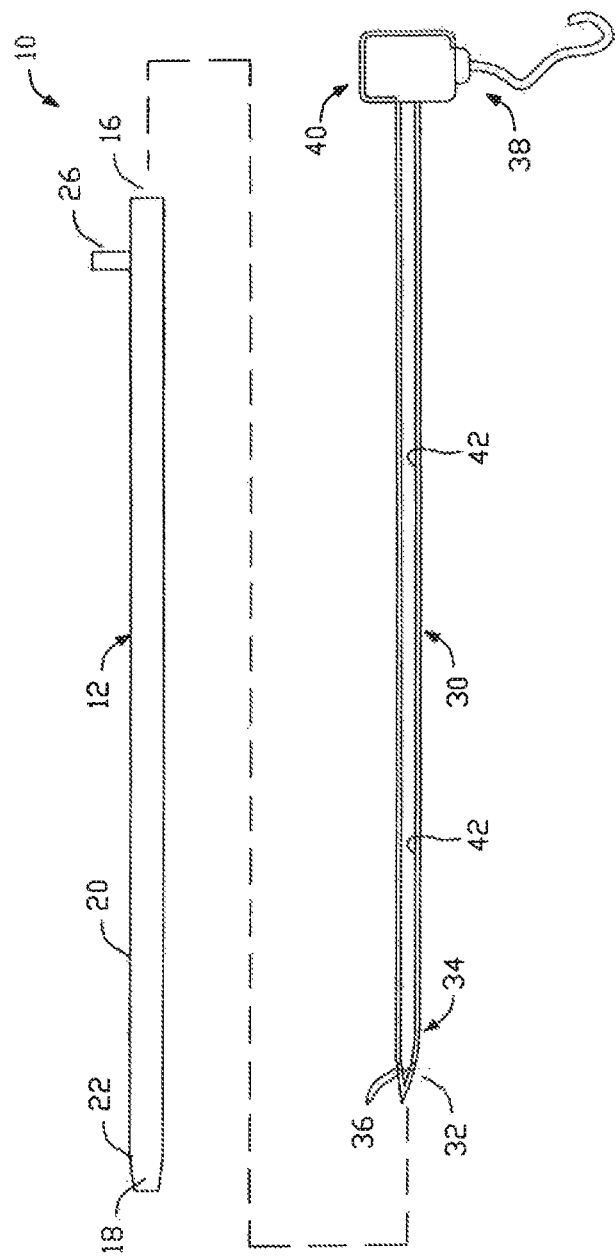
Figure 19:
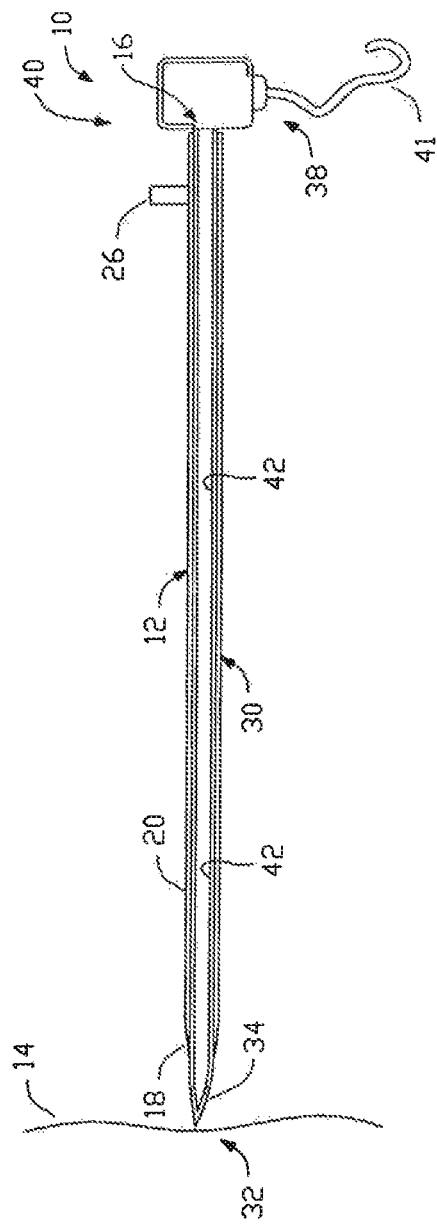
FIG. 19 illustrates an assembled view of the apparatus illustrated in FIG. 18.

FIGS. 13-18 illustrate ultrasonograms and drawings of various phases in the progress of a fascia iliaca block. In FIG. 13, the second lighter band from the top is the fascia lata. The third lighter band from the top is the fascia iliaca. FIG. 14 illustrates how under ultrasound guidance the introducer 30/sheath 12 (needle 30/sheath 12) is first introduced generally perpendicularly and then turned horizontally toward the proximal thigh. FIG. 15 illustrates how under ultrasound guidance the sheath 12 is advanced off the introducer 30 (needle 30). FIG. 16 illustrates in the lower left an outline of the margins of the echogenic sheath 12. FIG. 17 illustrates near the top of the image the fascia lata, just below the middle of the image the fascia iliaca and just below fascia iliac, near the bottom left of the image, the outline of the margins of the echogenic catheter 44.

Stimulating Needle/Non-Stimulating Catheter

Arrow International, Inc. (Teleflex Medical, PO Box 12600, Research Triangle Park, N.C. 27709) introduced an extremely popular stimulating needle/stimulating catheter (hereinafter sometimes the AC needle/catheter) several years ago. Placement of continuous nerve blocks with the AC needle/catheter required considerable skill. The technique involved placing an epidural needle next to a peripheral nerve. Inside the epidural needle is a stimulating catheter. This stimulating catheter consisted of a small plastic tubing with a wound, "slinky-like," metal coil inside. This stimulating catheter was connected to a battery capable of supplying a current. Specific muscle groups would be stimulated when the AC needle/catheter was near a peripheral nerve and the appropriate electrical impulse was given, identifying the location of the needle tip. This technique required knowledge of motor responses by muscle groups and their respective anatomy. Problems with this AC needle/catheter include the inner metal wire unwinding, the metal wire scraping nerves on removal, and expense to manufacture.

More recently, B. Braun Medical Inc., 824 Twelfth Avenue, Bethlehem, Pa. 18018 introduced a stimulating needle/non-stimulating catheter (hereinafter sometimes the BB needle/catheter). The BB catheter has the appearance of lightweight monofilament fishing line. Advantages of the BB needle/catheter are the lack of metal in the catheter, which could lead to a post-operative neuritis, and its case of use with ultrasound. Anesthesiology residents are now commonly trained with ultrasound guidance for peripheral nerve blocks. Many practicing anesthesiologists are working to learn ultrasound guided nerve blocks. There are, however, some shortcomings with the BB needle/catheter. The BB catheter is threaded through a small, perforated opening in the BB needle. The BB catheter can be difficult to advance through the BB needle because the BB catheter is very light in weight, flimsy and insubstantial. The end of the BB catheter tubing is attached by a catheter clip device which is not of a particularly robust design. This catheter clip device frequently pulls off the very light weight catheter, becoming contaminated in the process.

Both the AC needle/catheter and the BB needle/catheter are placed inside an epidural needle and advanced. Both of these techniques require much dexterity on the part of the anesthesiologist.

Figure 2:
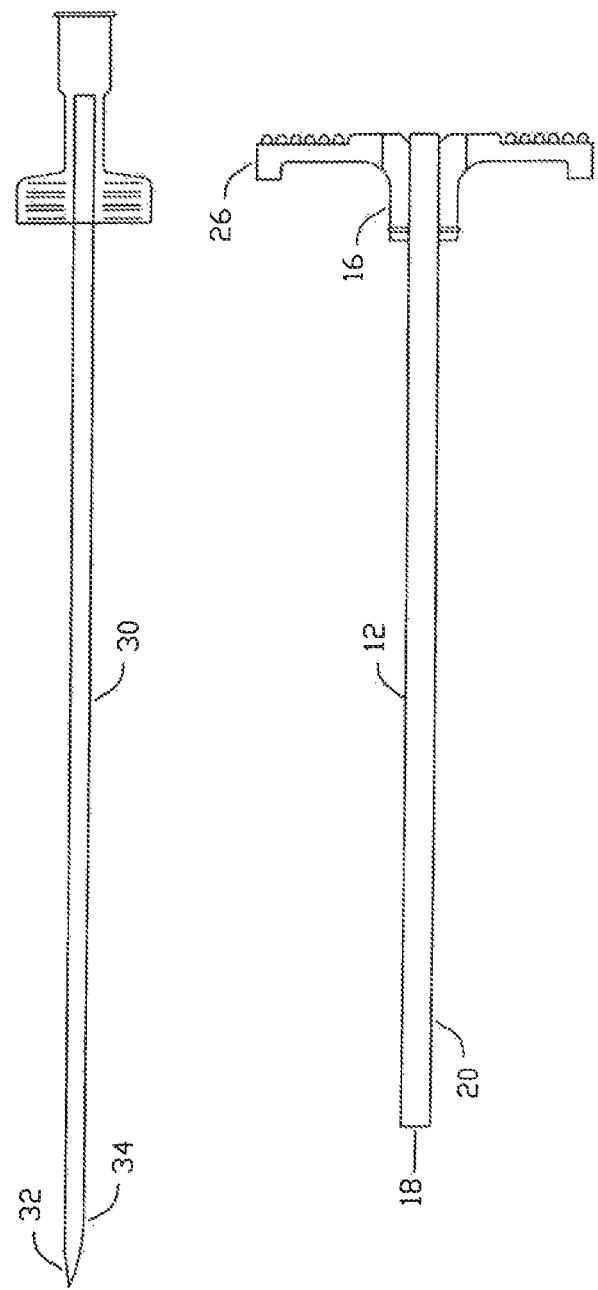
FIG. 2 illustrates the needle and sheath illustrated in FIG. 1 disassembled.
Figure 3:
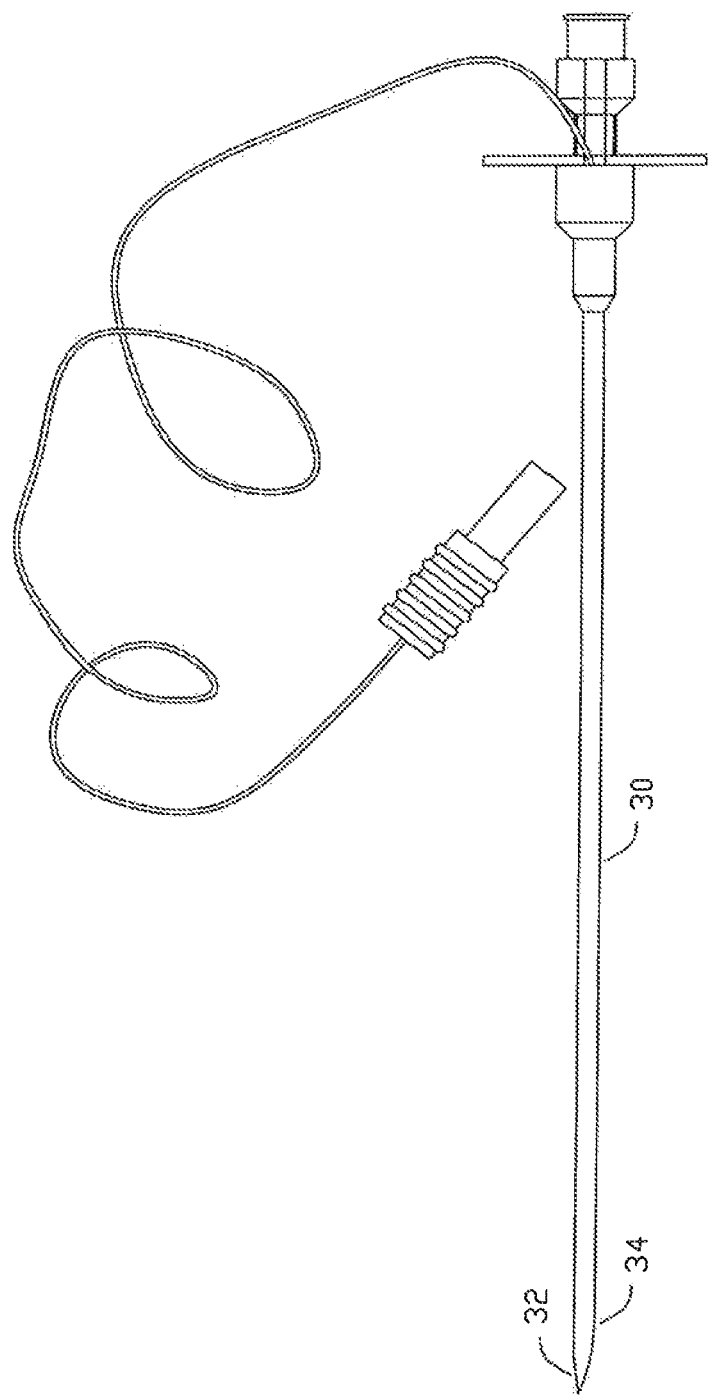
FIG. 3 illustrates a needle/sheath assembly. The surface of the needle is electrically insulated down to within a centimeter or so of its tip, and a conductor is attached to its proximal end to permit attachment to a nerve stimulator.
Figure 4:
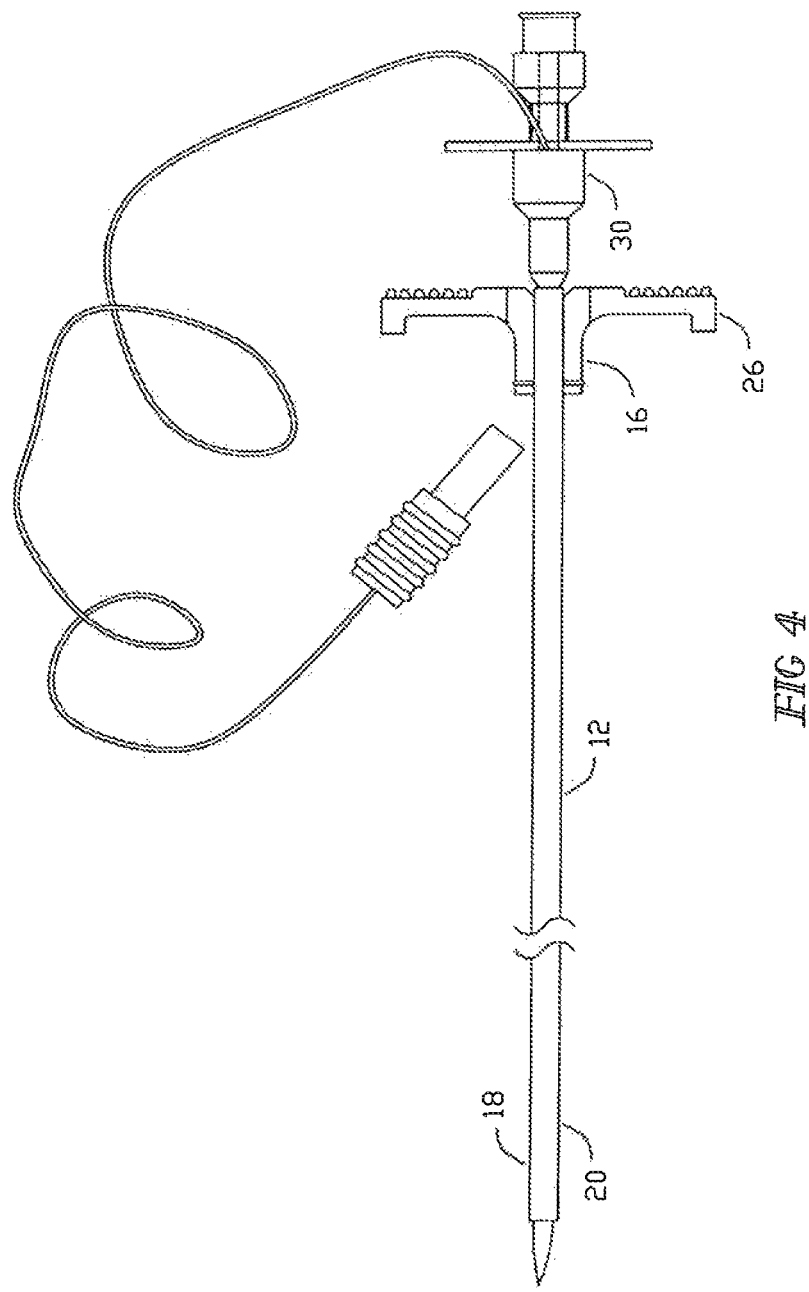
FIG. 4 illustrates the assembly illustrated in FIG. 3 assembled into a sheath.
Figure 5:
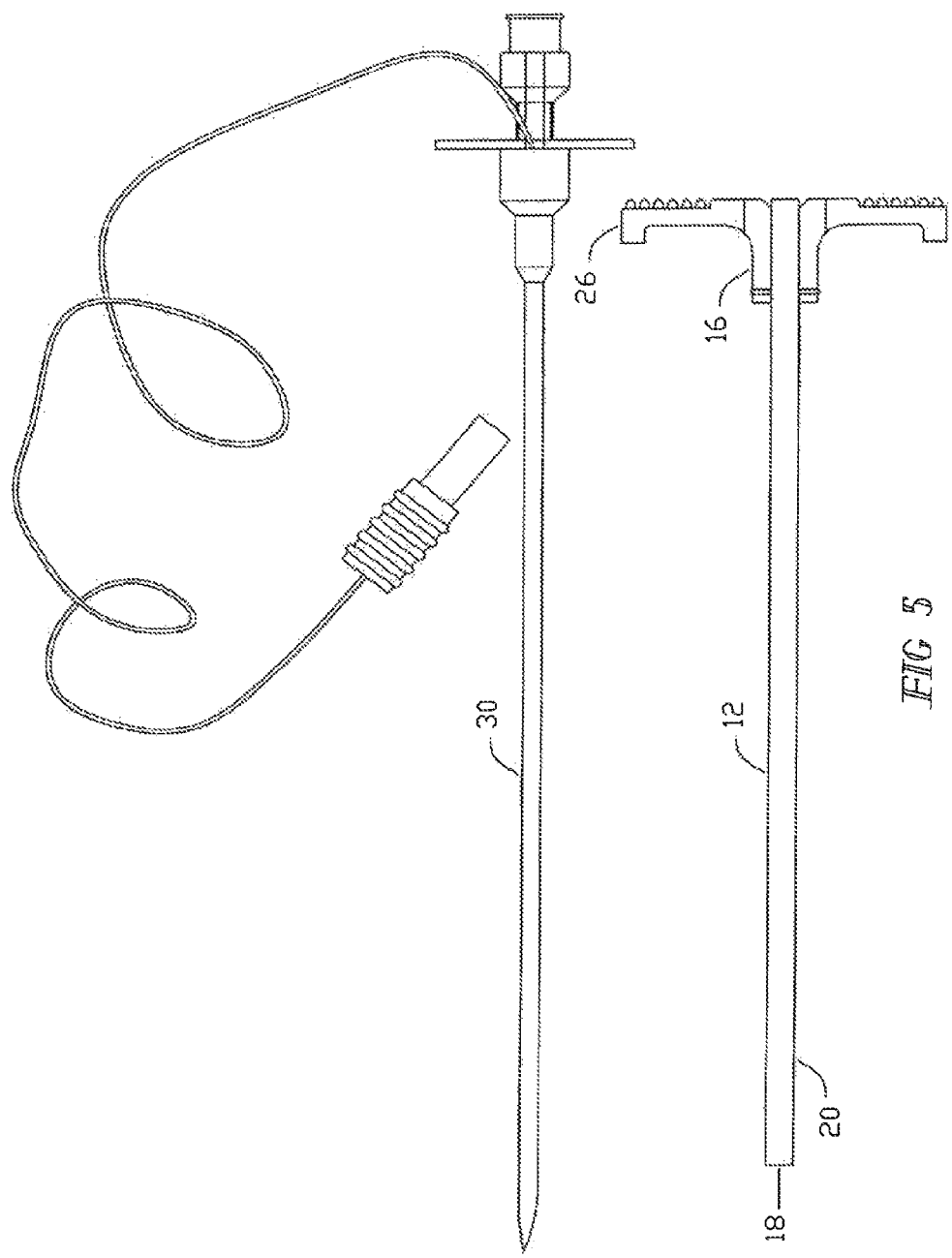
FIG. 5 illustrates the assembly illustrated in FIG. 3 removed from the sheath.
Figure 6:
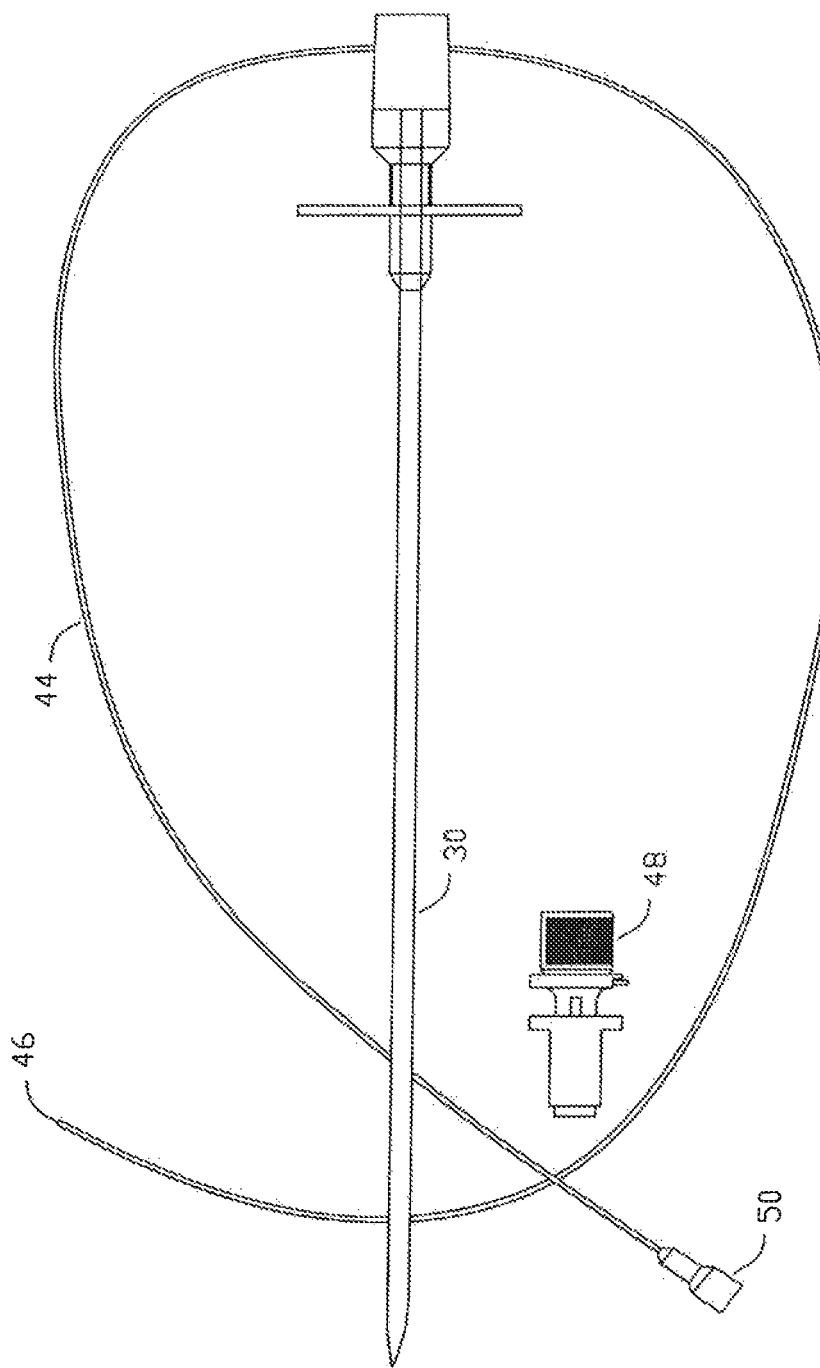
FIG. 6 illustrates a needle and a catheter with the hub for connecting the catheter to an infusion pump removed.
Figure 7:
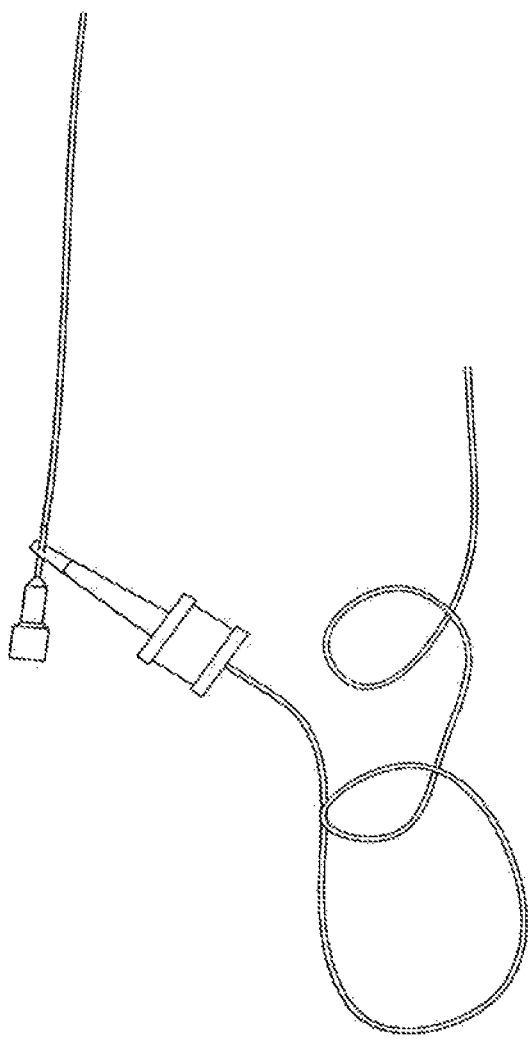
FIG. 7 illustrates a stimulating clip attached to the proximal end of a wire which extends through a catheter.
Figure 8:
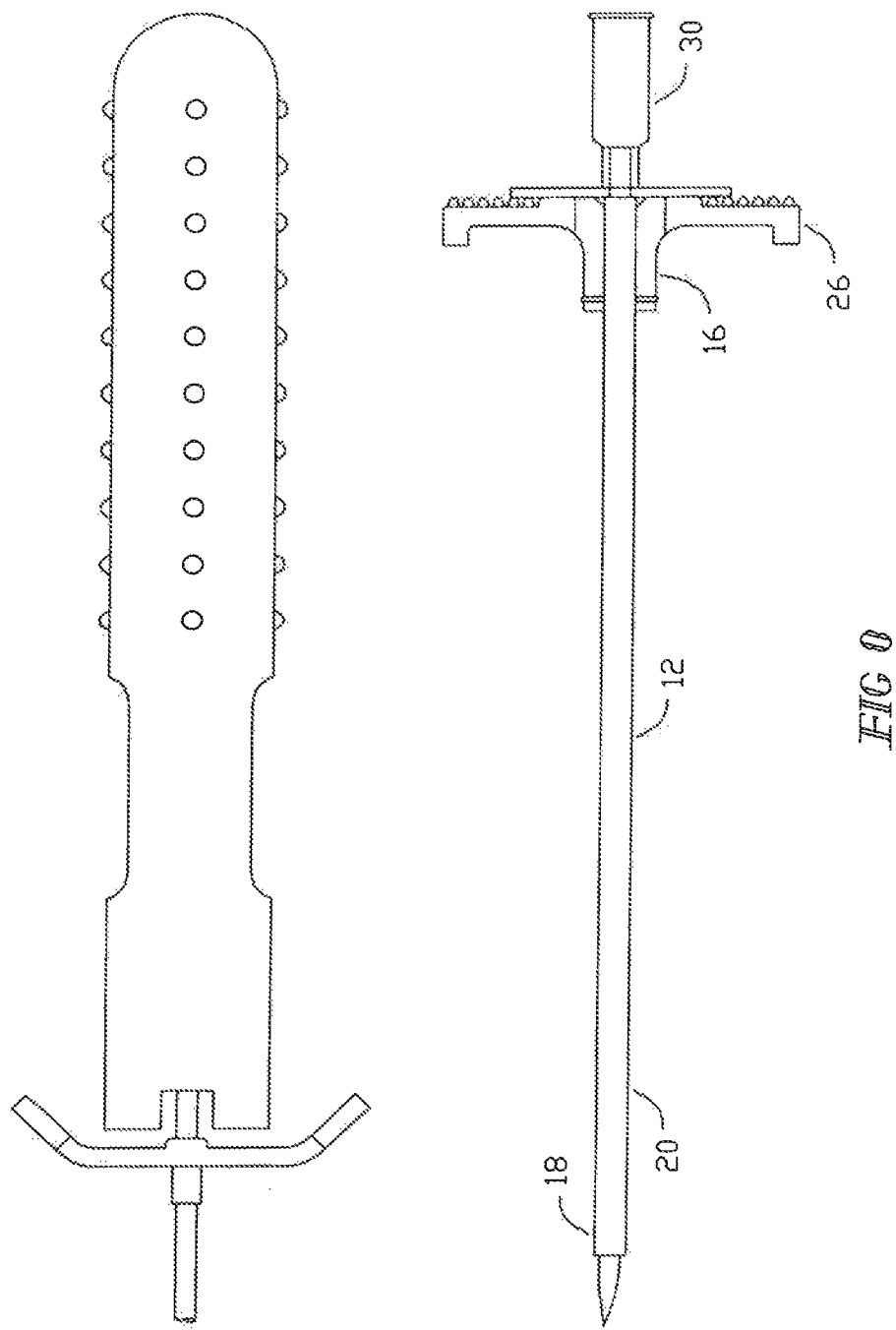
FIG. 8 illustrates a prior art rib fracture kit and the inventive introducer/sheath (needle/sheath), in this case with a 6 inch (about 15.2 cm.) needle and a 5 inch (about 12.7 cm.) needle; although the illustrated needle is a cutting type needle, a non-cutting (epidural style) needle is contemplated.
Figure 9:
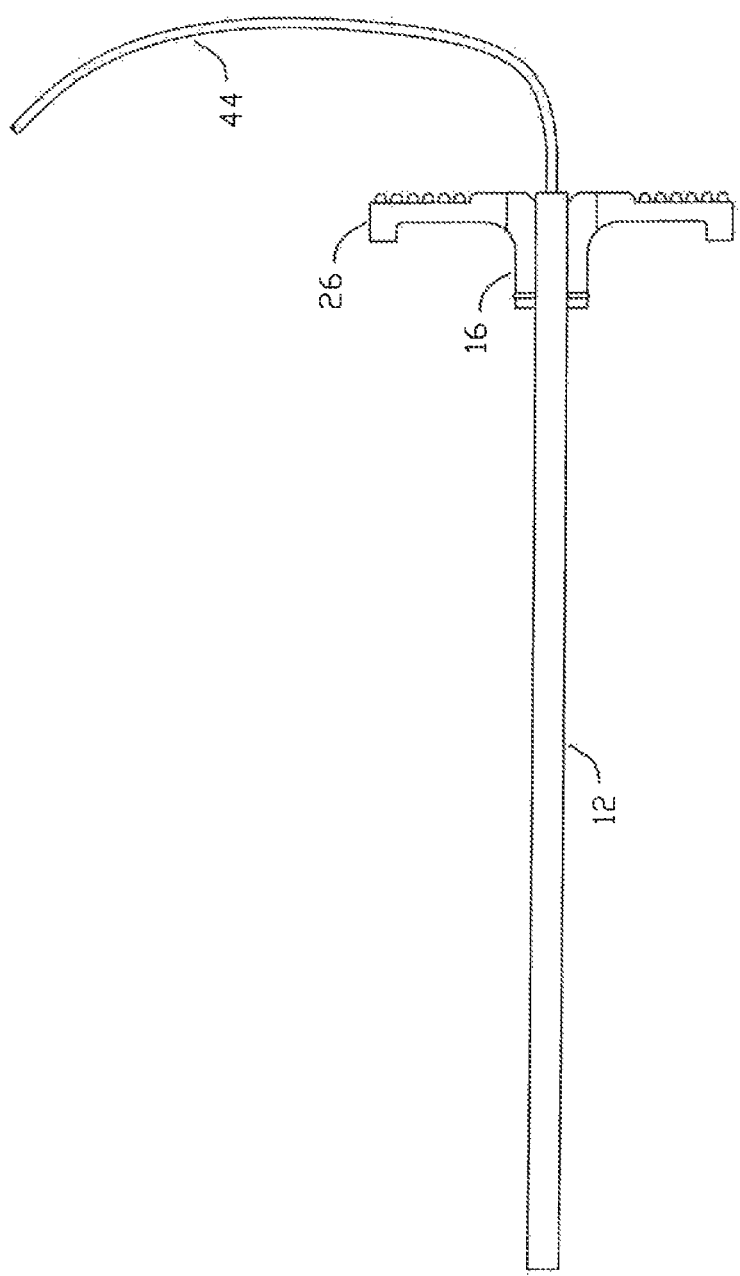
FIG. 9 illustrates a sheath with the introducer (needle) removed and a catheter threaded into the proximal end of the sheath.
Figure 10:
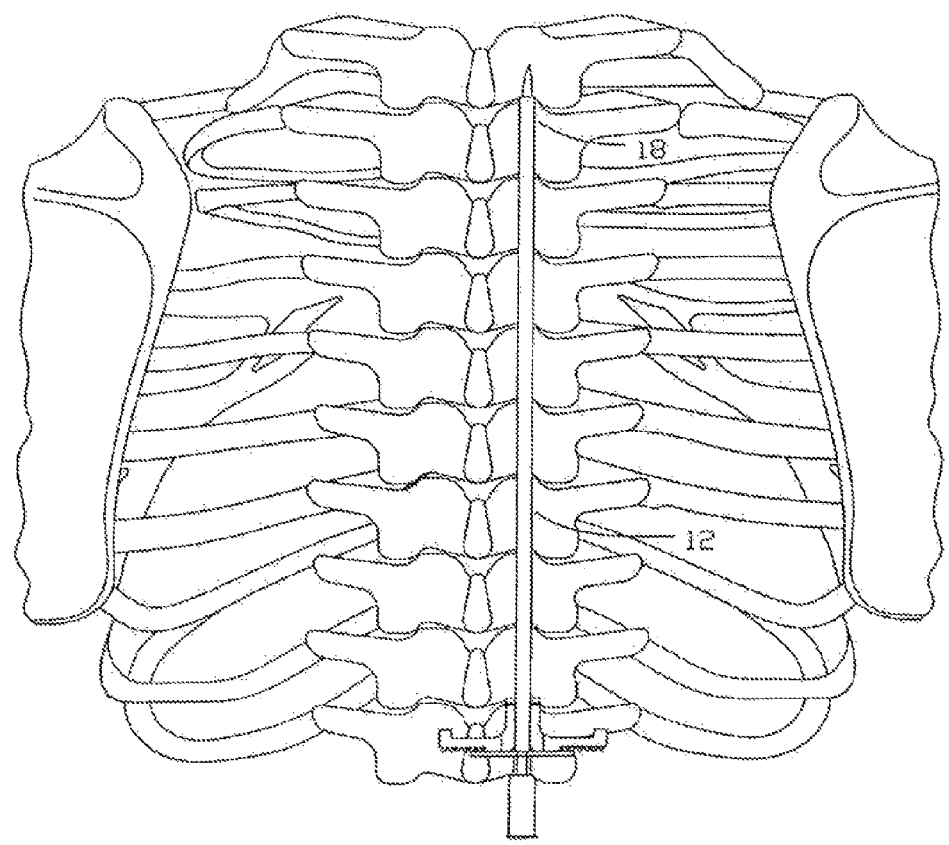
FIG. 10 illustrates a dorsal view of a rib cage illustrating the method for paravertebral block.

According to the inventive technique, an epidural needle 30 is placed inside an introducer sheath 12. See FIG. 1. The surface of the needle 30 is treated, for example, by coating with an electrically insulative material, down to within a few millimeters of its tip. This permits very accurate assessment of where the tip is when a current is applied, for example, via the clip, to the needle 30. Using the sheath 12 reduces the skill required to place a peripheral nerve catheter. The catheter I have selected is very robust and difficult to contaminate. A length of extension tubing is attached to the epidural needle. See FIG. 2. The needle/sheath 12 is directed under ultrasound guidance to a target peripheral nerve. A stimulating clip is attached to the epidural needle and the stimulator is used to confirm the placement performed by ultrasound. See Figs. The needle is bolused with an appropriate local anesthetic, and the epidural needle is removed.

Illustratively, two or three different sizes of needles and sheaths 12 will permit the anesthesiologist to perform the eight or nine common nerve blocks. Initially, kits will be directed at all of the orthopedic peripheral nerve blocks. There would likely be four kits containing similar components. Differences will be, for example, in the lengths of the stimulating needles.

Generally, each kit will include an epidural needle, a first introducer sheath 12, a second introducer sheath 12', a continuous nerve catheter, a drape, extension tubing, and a stimulator clip and electrically conductive wire or cable. Further details of illustrative components are as follow:

1) The stimulating needles are epidural needles that are insulated down to within a centimeter or so of their distal tips. Insulating the needle permits electrical stimulation from only the distal end. It is currently contemplated that kits will be available with stimulating needles in the following lengths: about 6.4 cm (about 2.5 inches); about 8.0 cm (about 3.5 inches); about 11.4 cm (about 4.5 inches); and, about 14 cm (about 5.5 inches). The stimulating needles have centimeter markings along the length of the needle. An example of this type of needle comes from Arrow kit ref SJ-05501.

2) A suitable connecting cable to attach to a peripheral nerve stimulator comes from Arrow kit ref AB-05060. The cable could come already attached to the needle.

3) Two introducer sheaths 12, 12' are currently contemplated. The sheath 12 for the stimulating needle will be about two centimeters (about 0.8 inch) shorter than the length of the stimulating needle. All of the stimulating needles will use an introducer sheath 12 similar to the one from I-Flow's (I-Flow Corporation, 20202 Windrow Drive, Lake Forest, Calif. 92630) soaker kit, ref. PM010, part#5001729. A second introducer needle 30' and sheath 12' are required to locate the non-stimulating catheter away from the surgical field. This second introducer sheath 12' is similar to the one from I-Flow's soaker kit, ref. PM010, part#5001729. The introducer sheaths 12 and the non-stimulating catheters should be made as echogenic as materials and manufacturing methods permit to facilitate location.

4) Two non-stimulating catheters are provided. One has an approximately 2.5 cm (about one inch) distal soaker region similar to the one in I-Flow's soaker kit, PMO-30. Another similar catheter is the one from Arrow's flextip epidural kit, ref. SJ-05501.

5) Extension tubing should be similar to the tubing from Havel's (Havel's Incorporated 3726 Lonsdale Street Cincinnati, Ohio 45227) echogenic needle, EBA-21100. The extension tubing illustratively is about 75 cm (about 30 inches) long.

6) An illustrative drape is Arrow drape product #CD-00001. Illustratively, the drape will have a rectangular, circular or oval opening, although a rectangular opening is currently thought to provide the greatest flexibility.

In order to get the mechanism for introducing anesthetic out of the surgical field, a second introducer needle 30'/sheath 12' is placed through the original puncture site and directed away from the surgical site. A continuous nerve catheter is placed through the second sheath 12', into the original sheath 12 and advanced, for example, two centimeters past the distal end 18 of the first sheath 12. Both introducer sheaths 12, 12' are removed and a sealant, such as Dermabond® liquid skin adhesive, applied to both puncture sites. All extra tubing is secured in a sterile dressing. The nerve catheter is bolused by the anesthesiologist and confirmed by ultrasound.

Figure 29:
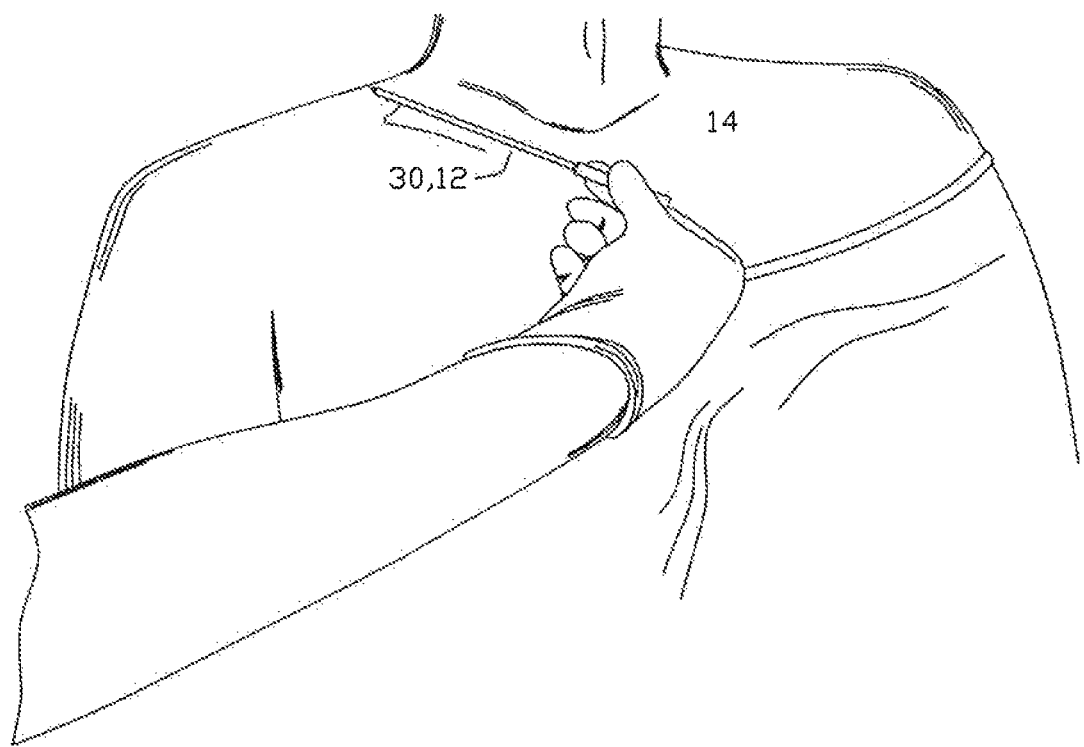
Figure 30:
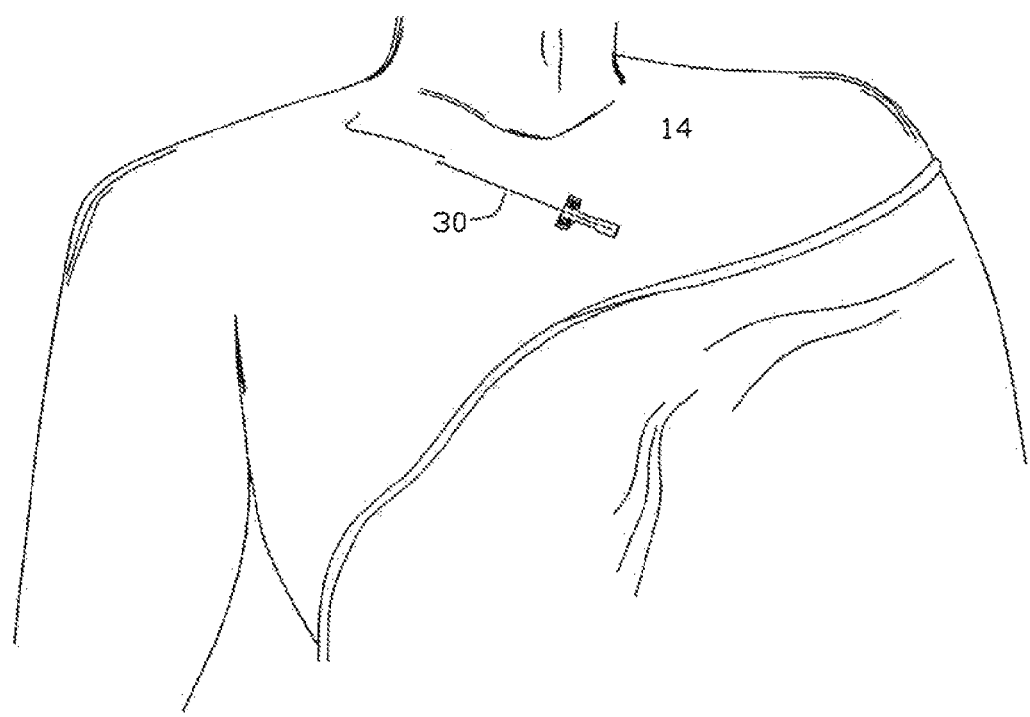
Figure 31:
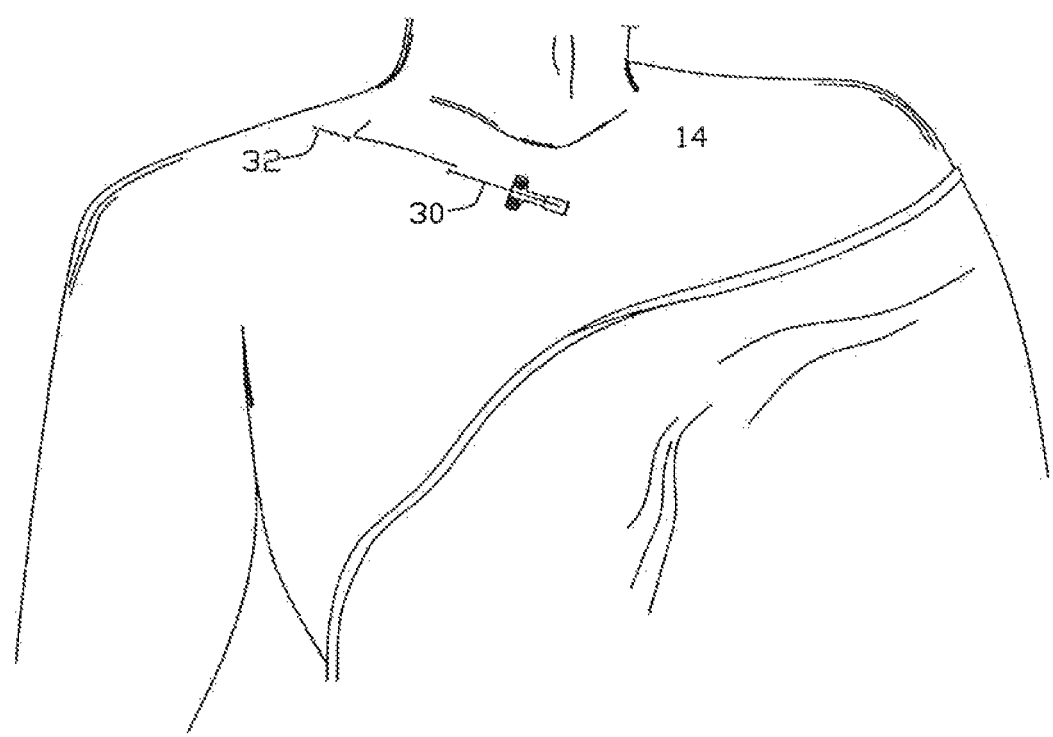
Figure 32:
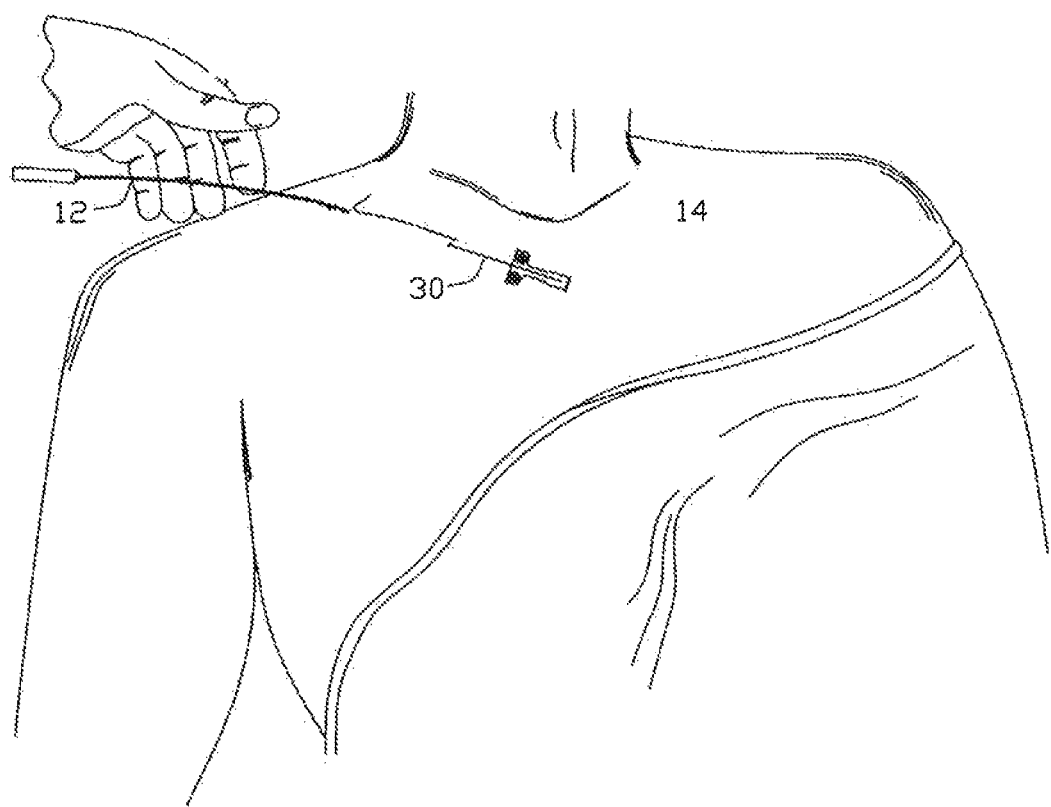
Figure 33:
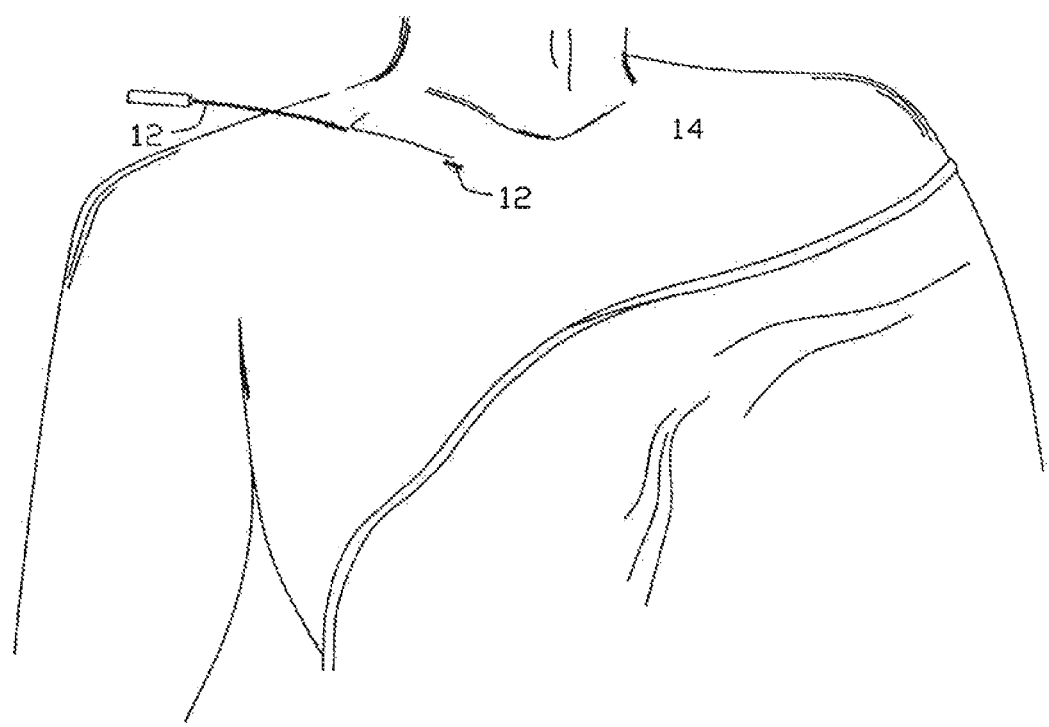
Figure 34:
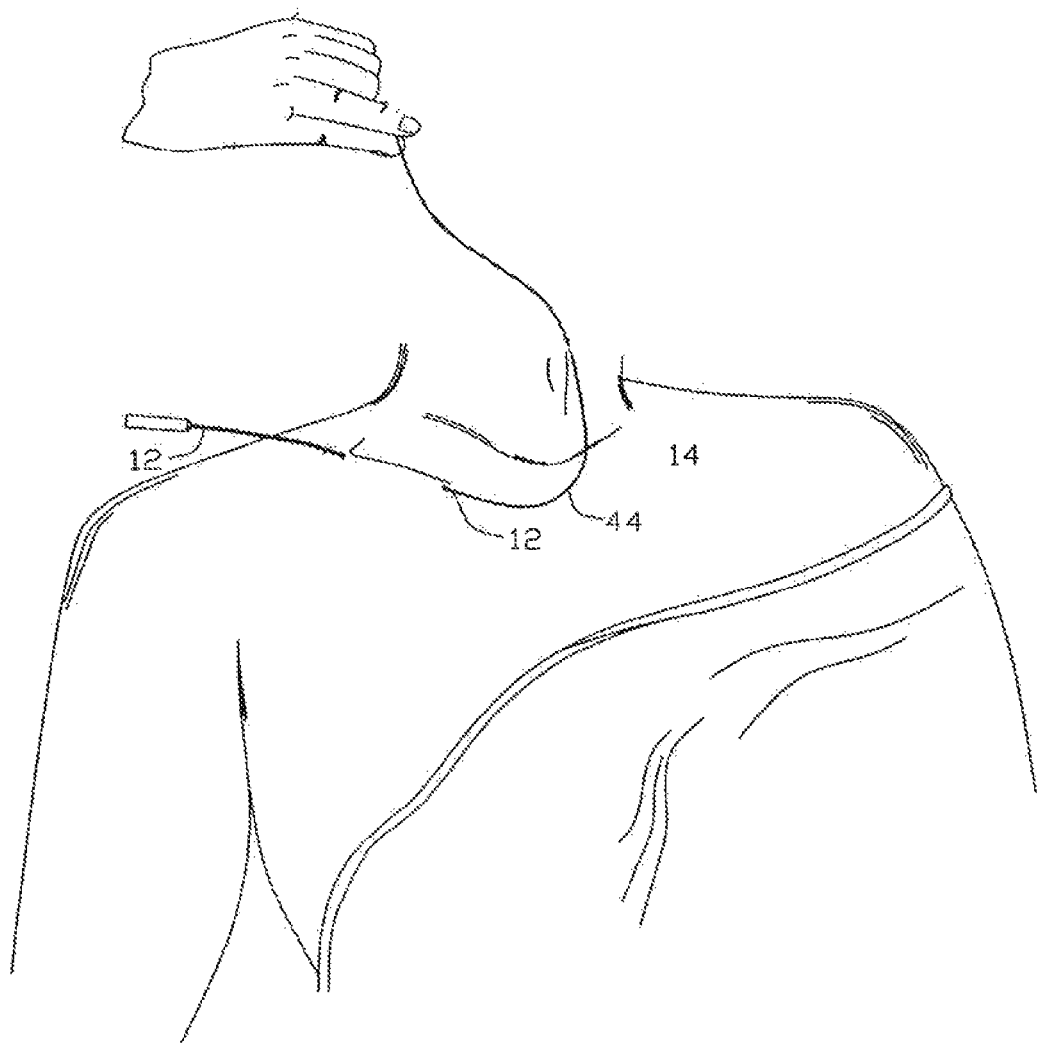
Figure 35:
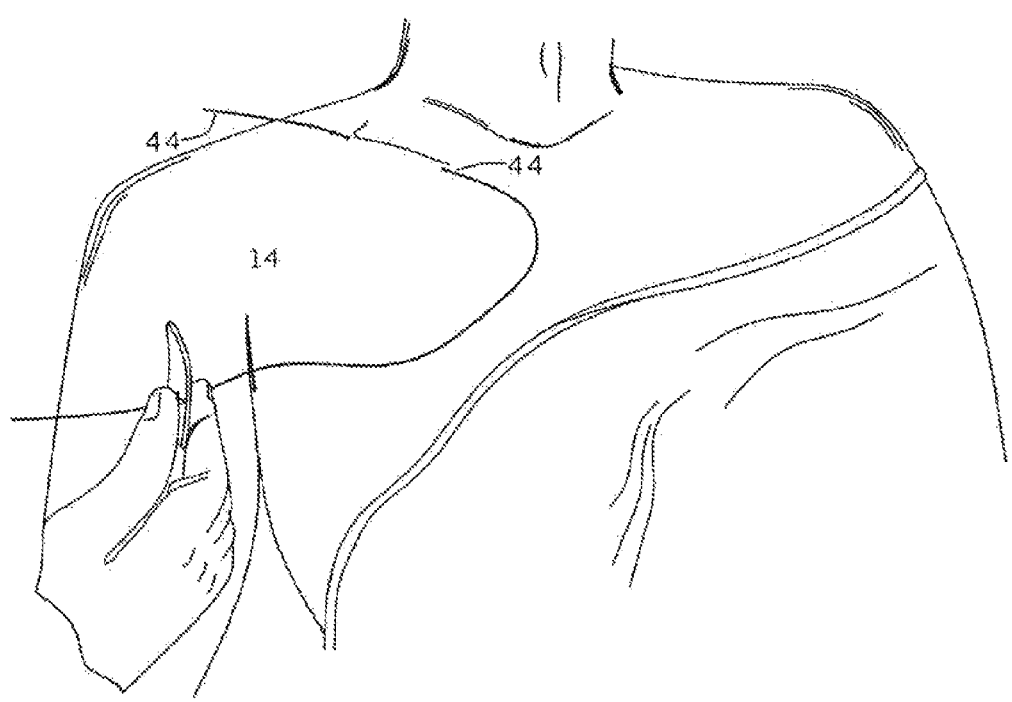
Figure 36:
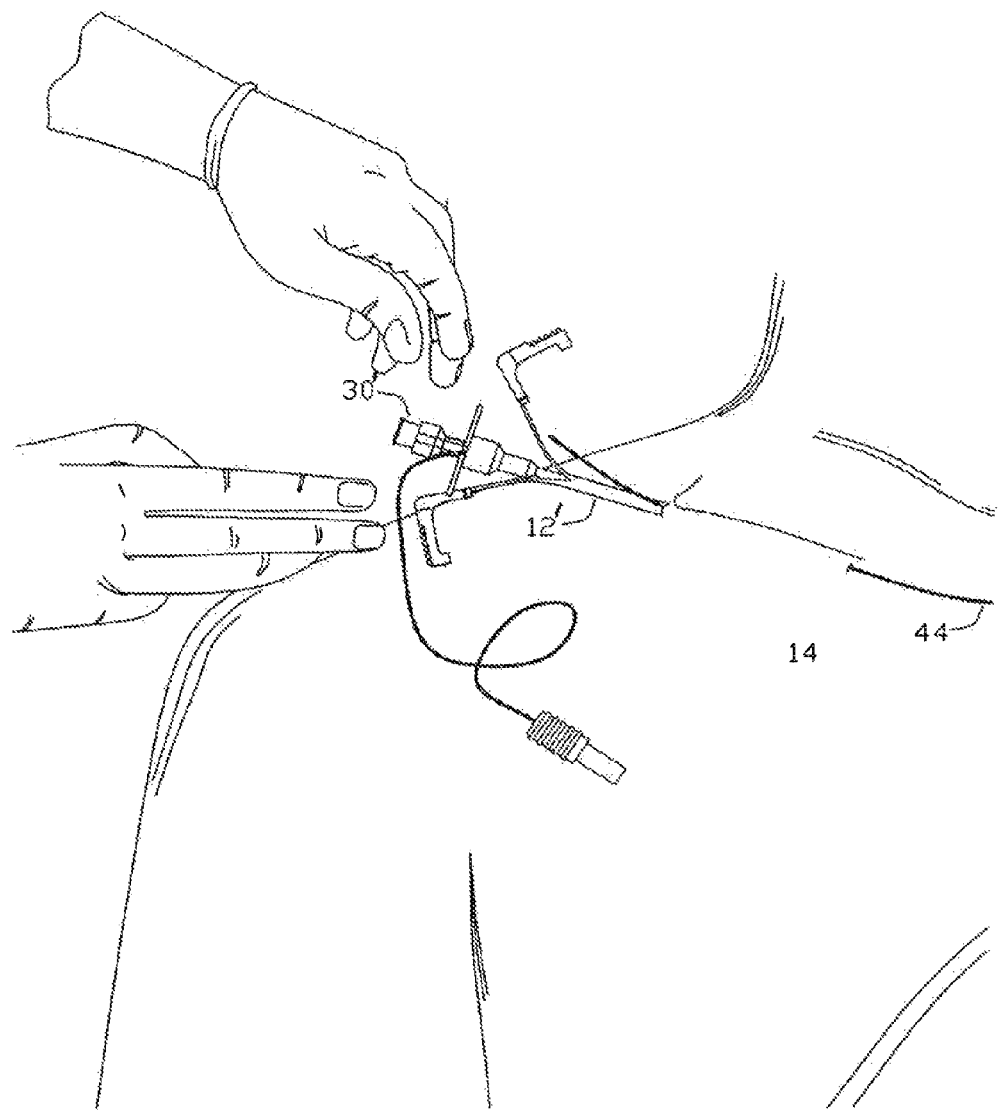
Figure 37:
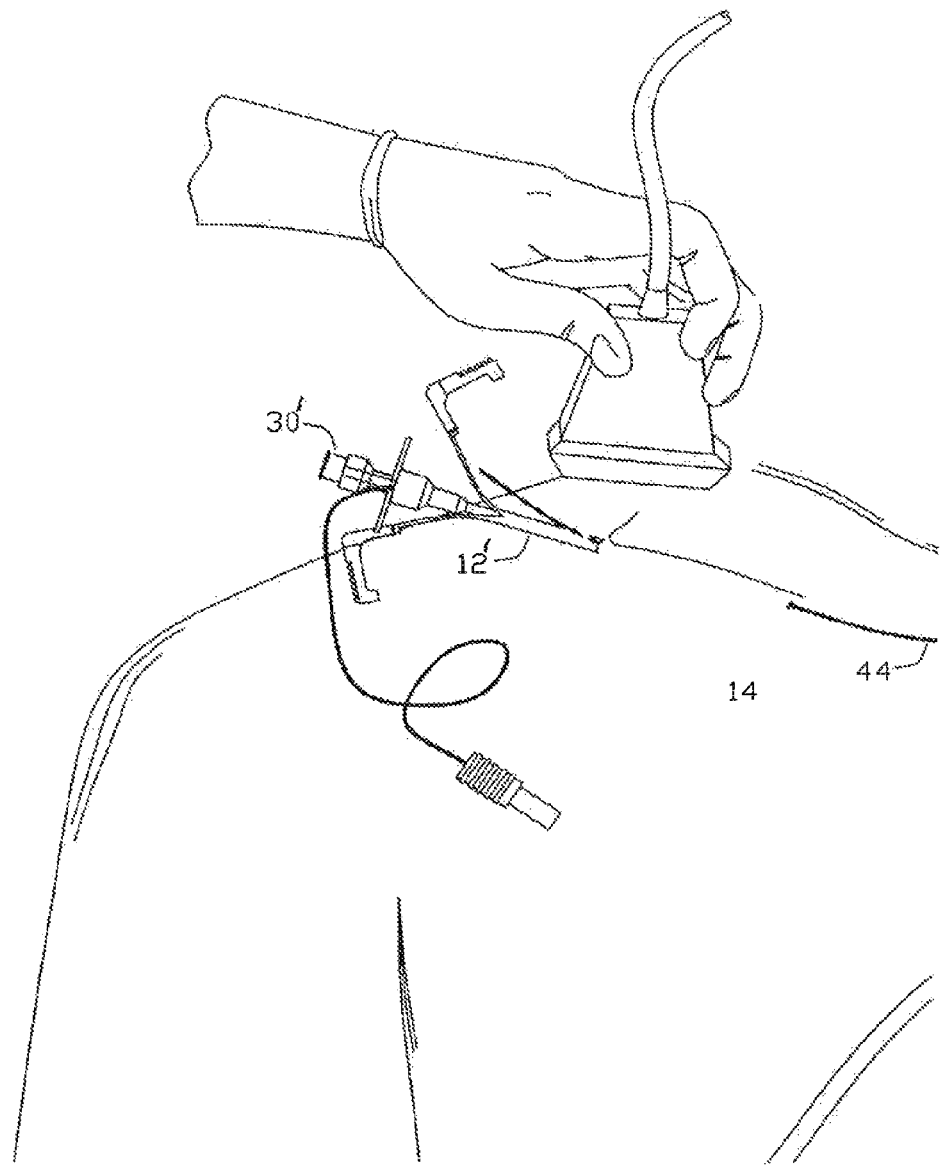
Figure 30:
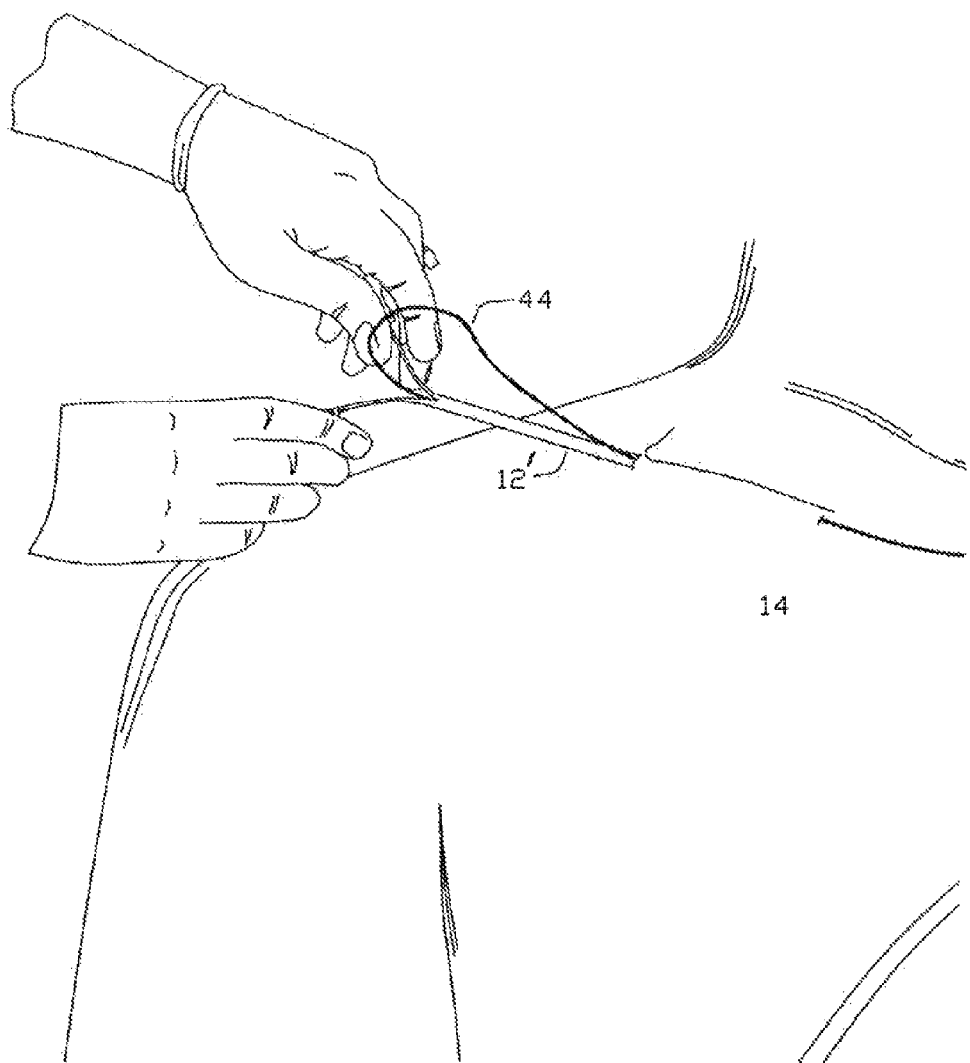
Figure 39:
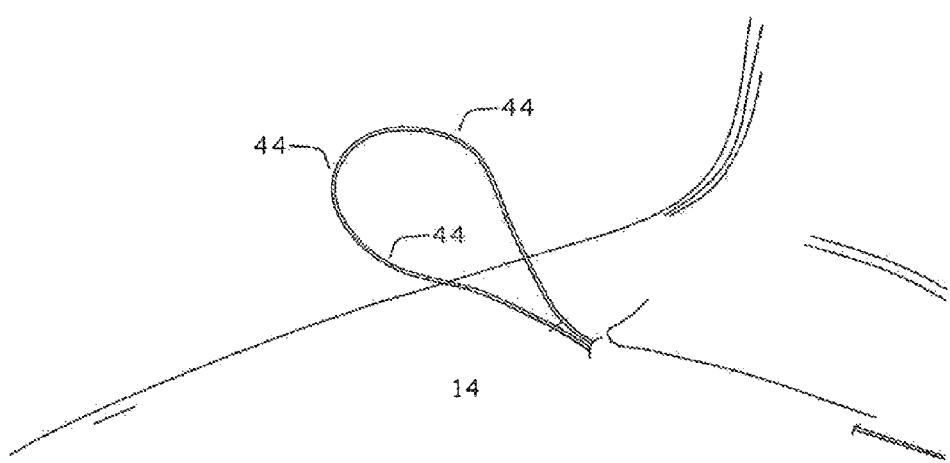

FIG. 28 illustrates an area above the clavicle of a patient 14 with a surgical drape. FIG. 29 illustrates a first (tunnel) needle 30/sheath 12. FIG. 30 illustrates the first (tunnel) needle 30 being inserted under the patient 14's skin with the distal end 32 emerging (FIG. 31) at a predetermined marked site where a second needle 30'/sheath 12' will subsequently be inserted. In FIGS. 32-33, the first (tunnel) sheath 12 is placed over the distal end of the tunnel needle 30 and both are withdrawn, pulling the tunnel sheath 12 back through the tunnel made by the tunnel needle 30. A first catheter 44 is advanced through the first (tunnel) sheath 12 until first catheter 44 reaches the opposite end of the tunnel. In FIG. 35, the first (tunnel) sheath 12 is then removed. The second needle 30'/sheath 12' is then advanced into the same orifice that was created by the distal end of the tunnel needle 30/sheath 12 with the aid of ultrasound visualization (FIGS. 36-37), and the nerve block is performed as described above. Referring to FIG. 38, the second needle 30' is removed, leaving the second sheath 12' in the patient 14 with its distal end 18 adjacent the nerve bundle to which the block has just been administered. The distal end 46 of the first catheter 44, which is protruding from the site where the block has been administered, is inserted into the proximal end 16 of the second sheath 12' and advanced down the second sheath 12' to the location of the block with the aid of ultrasound visualization as necessary. The second sheath 12' is then peeled back and removed. Referring to FIG. 39, the loop of the first catheter 44 extending from the site is then pulled back through the tunnel by pulling on the proximal end 50 of the first catheter 44. The first catheter 44 is thereby secured in place under the skin with its proximal access 48 away from the surgical field, ready to be connected to a source 52 of local anesthetic.

Open TAP Block

Having described how anesthesiologists can place continuous TAP blocks percutaneously, and can place them through a laparascope, LAP TAP, I have also had success placing TAP catheters in open abdominal procedures. A surgeon performing an open abdominal procedure can place a TAP block under direct vision. The surgeon can visualize the abdominal wall with a retractor and easily view the peritoneal cavity. Using the apparatus, the surgeon penetrates the patient 14's abdomen in an area of a typical posterior or subcostal TAP block. The surgeon, under direct vision, penetrates through the skin, fat, external oblique, internal oblique, and transversus abdominis muscles, and slides the apparatus along a plane parallel to and just above the peritoneum. From this point on, the process is similar to a LAP TAP. The distal end 18 of sheath 12 and tapered tip 32 are oriented in the belly of the transversus abdominis muscle. Local anesthetic is administered through tubing 41. If the surgeon has the apparatus too deep, the surgeon will see the apparatus penetrating the peritoneum, or if upon injection of local anesthetic, will notice the surface of the peritoneum is ballooning. The surgeon should then simultaneously withdraw the apparatus slowly out of the patient 14 and continue administering local anesthetic until a bulge is seen. See FIG. 11. The bulging indicates the transversus abdominis muscle is separating from the internal oblique. The process then proceeds in a manner similar to percutaneous TAP blocks, as described above. The introducer/dilator 30 is removed, the catheter 44 is advanced in the sheath 12, and the sheath 12 is removed leaving the catheter in the belly of the transversus abdominis muscle. The adapter 48 is attached to the external end 50 of the catheter 44 and then connected to an infusion pump 52 to begin the infusion.

Paravertebral Block, or PVB

A PVB is a complex peripheral nerve block that involves nerves immediately after they branch off from the spinal cord, and can be used in breast surgery, thoracotomy, rib fractures and the like. A PVB has many advantages over traditional spinal/epidural blocks. PVB generally does not cause hypotension, urinary retention, or lower extremity motor block. PVB is unlikely to cause neuraxial damage, epidural abscess, or hematomas. Pain control with PVB has been shown to be equal to traditional thoracic epidurals. Long term benefits for surgery patients have been observed. Specifically, breast surgery patients have been shown to experience less long term pain after mastectomy, and possibly a reduction in breast cancer recurrence if they receive a pre-incisional PVB. The most significant complication for anesthesiologists when placing PVB is pneumothorax. The main barrier for widespread use of PVB is the extremely limited number of anesthesiologists with training to perform this complex procedure. The described method and apparatus are intended to address these issues associated with PVB.

The parts required, and method for placement of the block are as follows. A para-spinous soaker catheter is to be placed 1.25-2.54 cm lateral to the spinous process of a patient 14. The parts include a six inch (about 15.2 cm), 17 gauge Tuohy epidural needle 30 (similar to, but slightly longer than BBraun product code E1745T, ref 332181), a 5⅞ inch (about 14.9 cm) tapered 22 para-spinous sheath 12 (similar to the sheath in I-Flow ref PM020 parts 5001730/101353400), a five inch (about 12.7 cm) multi-orifice para-spinous soaker catheter 44, 46 (similar to the soaker hose in I-Flow ref PM020 parts 5001730/101353400), intravenous extension tubing (such as Hospira 30 inch (about 76.2 cm) list no 12656-28), and plastic drape (similar to Arrow clear fenestrated drape product no. cd-00001). The epidural needle 30/para-spinous sheath 12 assembly is sometimes referred to hereinafter as a para-spinous apparatus or PSA and may be referred to by the reference numbers 30, 12.

Method

The procedure can be performed in a lateral decubitus or prone position. In the description that follows, it will be assumed that the patient 14 is in the prone position, and unilateral. The description is for a unilateral para-spinous catheter placement from T5 to C7 (vertebrae). The procedure can involve the entire thoracic vertebrae, thus requiring two catheters, one cephalad and one caudad, and may also be bilateral.

The patient 14 is placed in a prone position. C7 to T5 spinous processes are noted and external skin is marked. The patient 14 is prepped and draped. A sterile ultrasound probe is placed transverse to the spine and the depth of the transverse process and external intercostal muscle are noted at each level to be blocked. Local anesthetic is placed at T5, approximately 1.25-2.54 cm lateral from the T5 spinous process. The PSA 30, 12 is introduced at this site under the skin to a depth just above the external intercostal muscle. The PSA 30, 12 is then advanced cephalad, under ultrasound guidance at a depth just above the external intercostal muscle of each vertebra, maintaining constant lateral distance from the spinous process of about 1.25-2.54 cm. The PSA 30, 12 advancement is aided with intermittent injection of local anesthetic. The PSA 30, 12 advancement is stopped when C7 skin marker is reached. The epidural needle 30 is removed from the PSA 30, 12, and then the para-spinous multi-orifice catheter 44, 46 is advanced into the para-spinous sheath 12. The para-spinous sheath 12 is removed leaving the para-spinous catheter 44, 46 in proper position. The catheter 44, 46 is covered with sterile dressings, bolused with local anesthetic, and connected to an appropriate local anesthetic infusion device.

We have seen virtually pain free recovery after mastectomy, breast reconstruction, and axillary node dissection. This technique has also recently been used on a trauma patient who had 5-6 rib fractures after a fall from a horse. The patient was 99 percent pain free after receiving the described modified paravertebral block.

Figure 24:
FIGS. 24-27 illustrate ultrasonograms of various phases in the progress of a paravertebral block.
Figure 25:
Figure 26:
Figure 27:
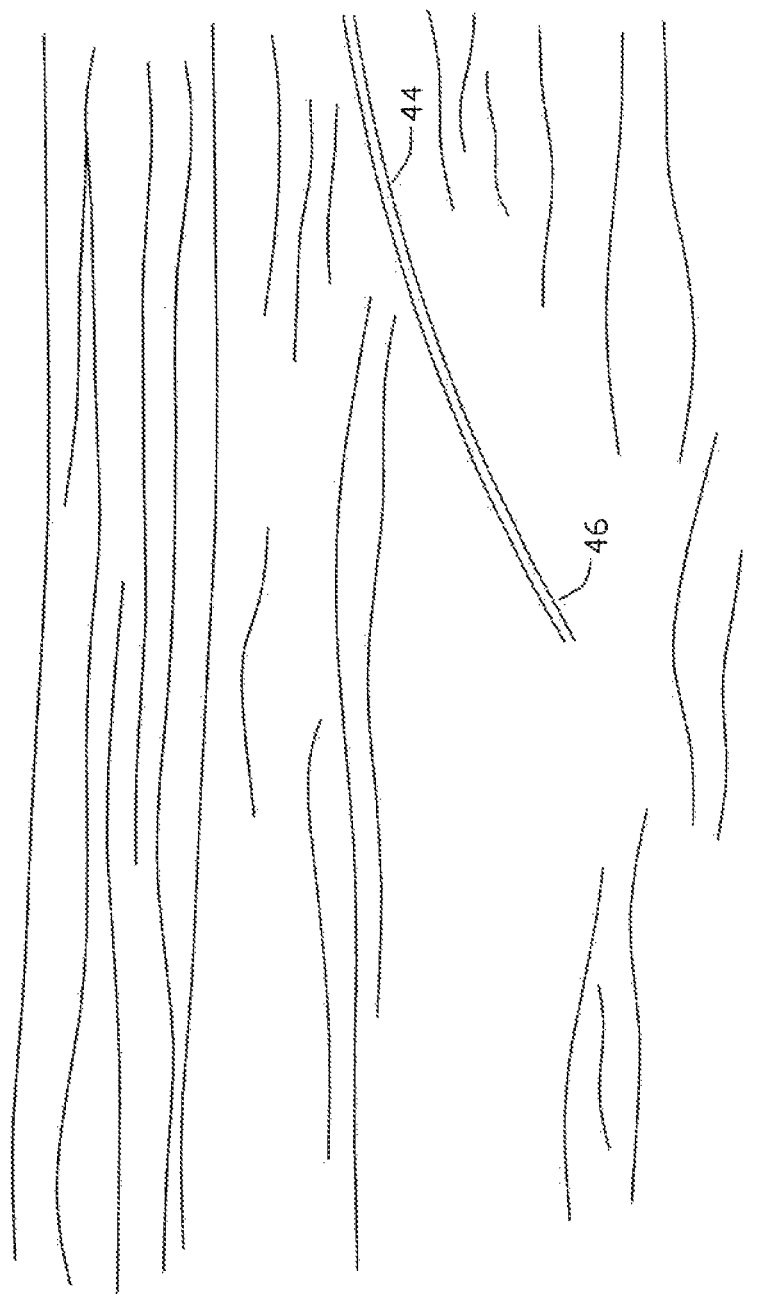
Figure 20:
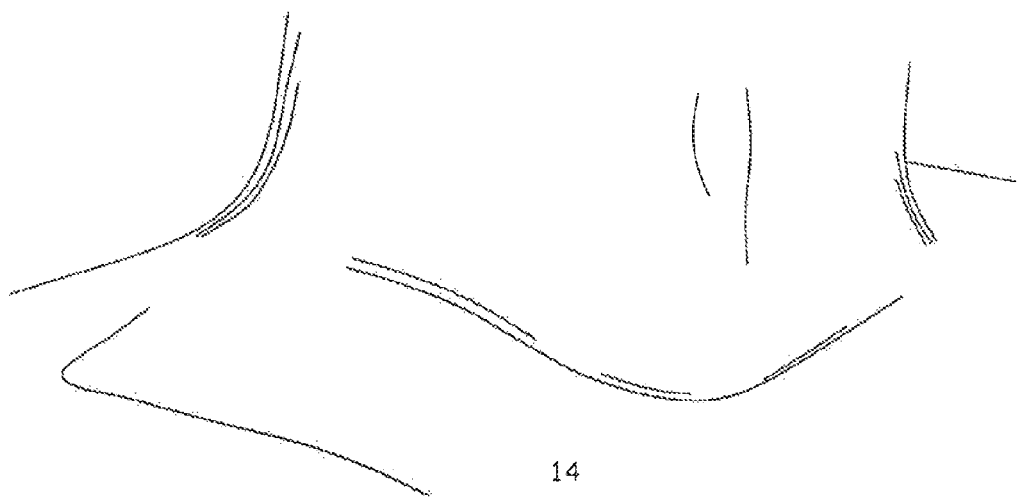

FIGS. 24-27 illustrate ultrasonograms of various phases in the progress of a paravertebral block. FIG. 24 illustrates the pleura of the lung (the white area at the bottom of FIG. 24), and just above it, the intercostal muscle. Entering from the right and just above the intercostal muscle, the introducer 30 (needle 30)/sheath 12 is visible. The target nerve bundle is to the left, below the center of FIG. 24. In FIG. 25, the introducer 30 (needle 30)/sheath 12 has been advanced and the tip 32 of the needle 30 has reached the nerve bundle. In FIG. 26, the needle 30 has been withdrawn, leaving the sheath 12 ready to receive the catheter 44. In FIG. 27, the catheter 44 has been advanced through the sheath 12 to adjacent the pleura (the lighter line at the bottom of FIG. 27), the sheath 12 has been removed, and local anesthetic is being administered. The local anesthetic is the darker area between the tip 46 of the catheter 44 and the pleura.

Other Blocks

Brachial plexus, sciatic, and saphenous nerve blocks are well documented in regional anesthesia books, articles, and on the Internet. All of these blocks require advanced medical knowledge pertaining to human anatomy and ultrasound techniques. The common theme is as follows: a target nerve plexus is visualized with an appropriate ultrasound unit; the patient 14 is prepped and draped; skin local anesthetic is given to the appropriate site; the apparatus 10 is placed in the appropriate area near the target nerve bundle; target site verification is performed by ultrasound or ultrasound complemented with nerve stimulation (assuming a stimulating Tuohy needle is the introducer/dilator 30); an appropriate local anesthetic is bolused through the introducer/dilator 30 and the introducer/dilator 30 is then removed, leaving the sheath 12 in close approximation to the target nerve bundle; an echogenic catheter 44 is then advanced to the distal end 18 of sheath 12 or until mild resistance is encountered and the sheath 12 is then removed. Sterile dressings are applied, an infusion pump 52 is connected to the catheter 44 and infusion of the local anesthetic commences.

Figure 20:
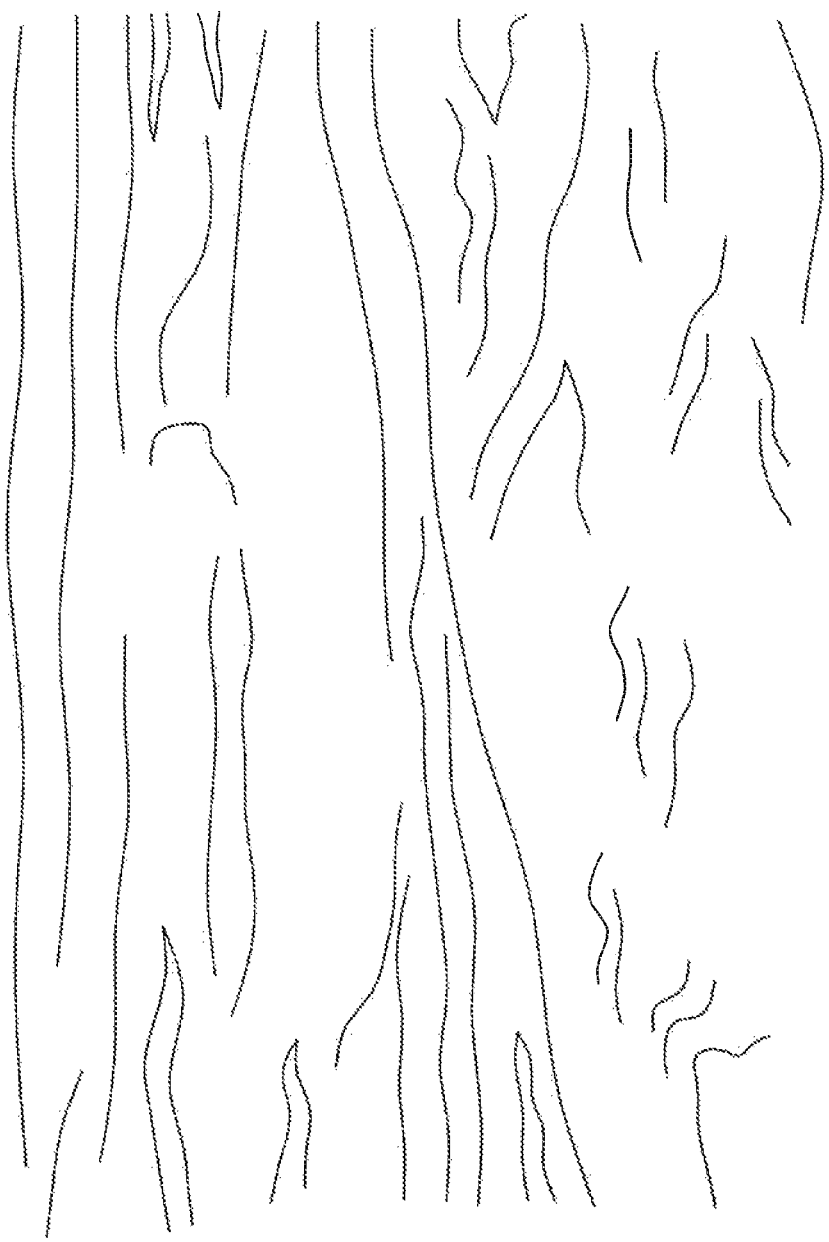
FIGS. 20-23 illustrate ultrasonograms of various phases in the progress of a supraclavicular block.
Figure 21:
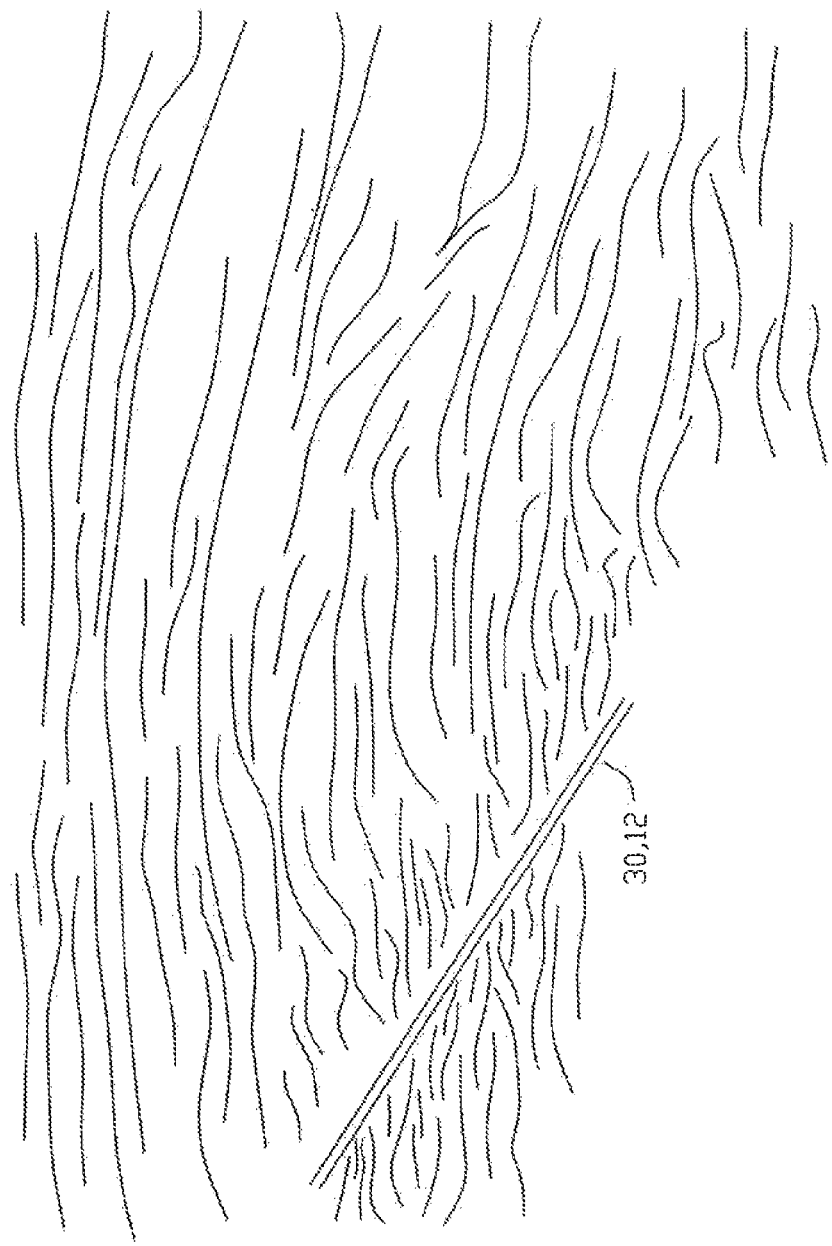
Figure 22:
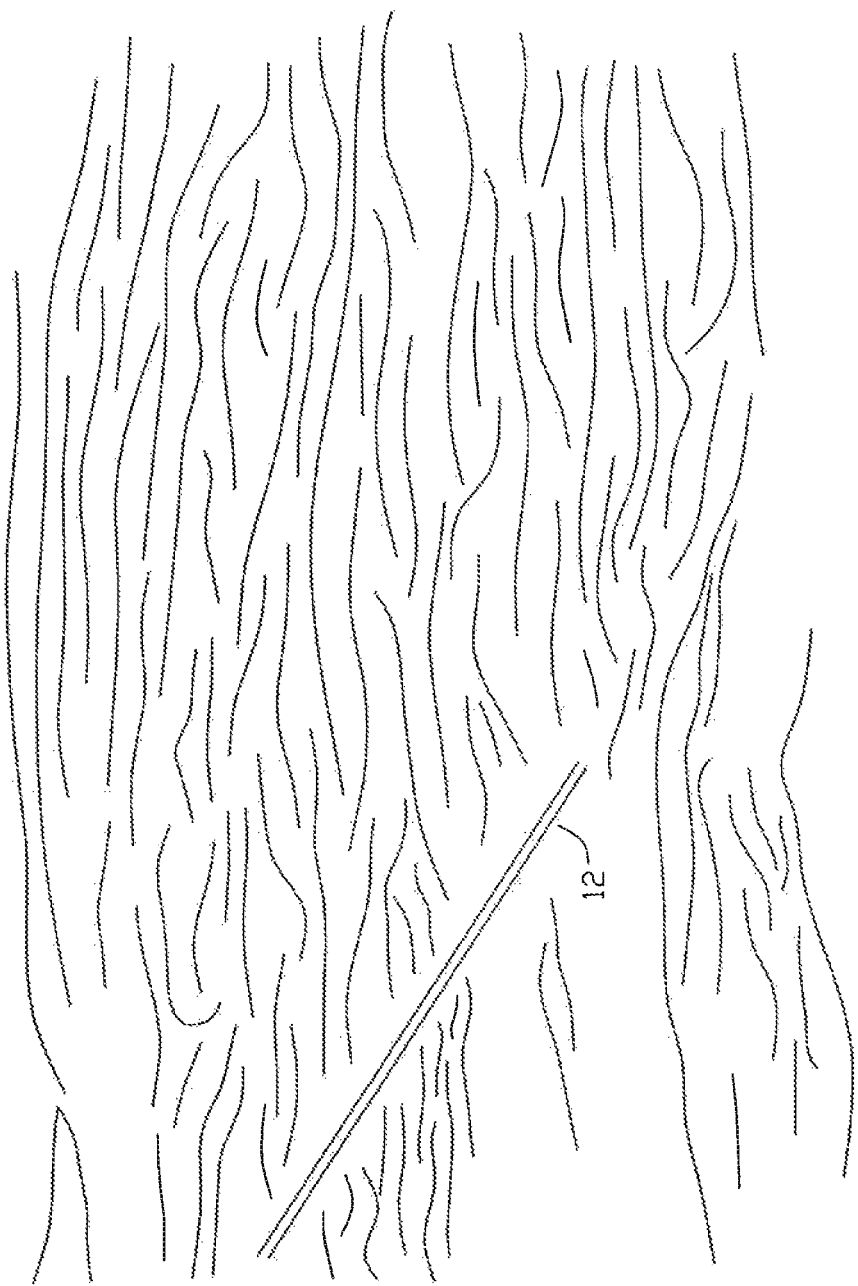
Figure 23:
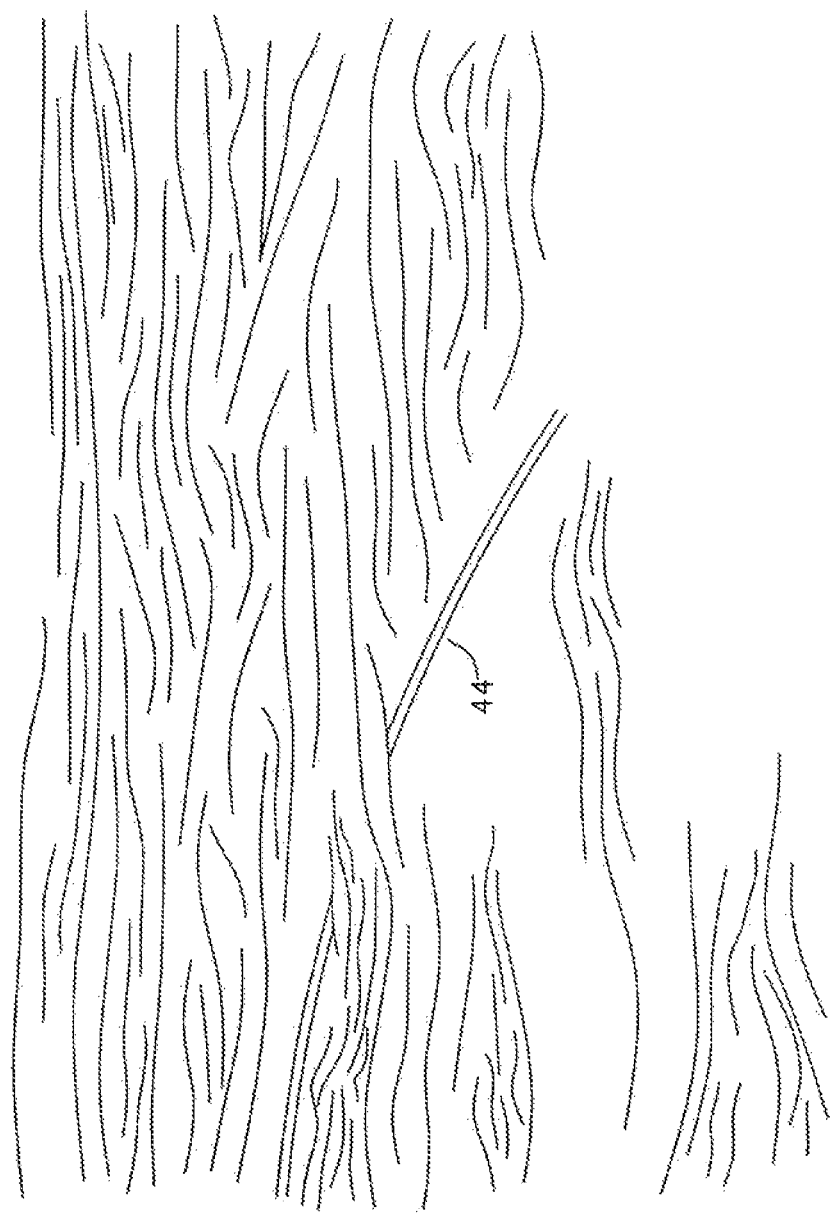

FIGS. 20-23 illustrate ultrasonograms of various phases in the progress of a supraclavicular block. In FIG. 20, the white lines which extend approximately through the center of the figure mark the fascia of the middle scalene. The dark ovals in the lower portion of the drawing, center and right illustrate nerve bundles and the subclavian artery. FIG. 21 illustrates the introducer 30 (needle 30)/sheath 12 entering from the upper left toward the nerve bundle. FIG. 22 illustrates the sheath 12 after withdrawal of the introducer 30 (needle 30), introduction of the catheter 44 and introduction of an amount of local anesthetic. The local anesthetic is the dark area in the lower middle of FIG. 22. FIG. 23 illustrates the catheter 44 in place in the pool of local anesthetic.

Adductor Canal Block or ACB

The adductor canal (subsartorial canal or Hunter's canal) is about 15 cm in length and is a narrow, fascial tunnel in the thigh. The adductor canal is located deep to the middle third of the sartorius muscle. The adductor canal provides an intermuscular passage through which the femoral vessels pass to reach the popliteal fossa, where these vessels become popliteal vessels. The adductor canal begins about 15 cm (about 6 inches) inferior to the inguinal ligament, where the sartorius muscle crosses over the adductor longus muscle. The adductor canal ends at the adductor hiatus in the tendon of the adductor magnus muscle. The saphenous nerve and, in part, the obturator nerve traverse the adductor canal. It is hypothesized that repeated administration of local anaesthetic into this aponeurotic space could provide sensory-only pain management for knee surgery, thus enhancing early ambulation after procedures like total knee replacement.

The adductor canal has been shown by MRI to be capable of holding about 30 ml or so of fluid, for example, local anesthetic. Blocks of the sensory nerve passing through the adductor canal using 0.2 percent ropivicaine have been achieved by administering 30 ml initial bolus and 6 ml/hour for maintenance. The approximately 6 ml/hour for maintenance can be reduced to the range of about 2-4 ml/hr after one day post op. Because the motor nerves are not anesthetized, there is no weakening of the quadriceps muscle. This reduces significantly the risk of injury during recuperation and promotes mobility, healing and recovery. The procedure requires ultrasound to place the soaker catheter accurately in the adductor canal. The procedure also requires a constant infusion pump post op to deliver the local anesthetic at initially 6 ml/hour or 2-4 ml/hr after one day post op. The technique has been verified on several patients undergoing, for example, unilateral total knee arthroplasty (hereinafter sometimes uni TKA), anterior cruciate ligament (hereinafter sometimes ACL) repairs, and knee manipulations (Patients post-knee surgery, such as total knee replacement, ACL repair, knee arthroscopy, and the like, may develop adhesions in the joint capsule. These adhesions can restrict full flexion and extension of the knee, resulting in decreased ability to walk correctly. Surgeons will occasionally treat these patients with "frozen knee"-like symptoms by manipulating the knee to full flexion and extension. This is a painful procedure and requires a general anesthetic. This manipulation procedure may cause severe pain after the adhesions are broken, and lead to decreased ability to walk. Surgeons may request a "sensory only" post-op block, such as an adductor canal, because it permits the patient to ambulate with minimal pain and continue physical therapy to avoid a recurrence of symptoms). Importantly, because this is a sensory nerve block only, and not a motor nerve block, there is no risk of quadriceps weakness. It is believed that most healthcare providers will prefer adductor canal blocks rather than femoral nerve blocks for these procedures.

Using an appropriate sterile technique, an adductor canal block can be accomplished using a 4 inch (about 10.2 cm) B. Braun Tuohy needle 30, with a 3½ inch (about 8.9 cm) I-flow sheath 12 (for example, of the type previously identified) placed over the needle 30. The needle 30/sheath 12 is connected to sterile IV tubing, attached to syringes of local anesthetic, and handed to an assistant. The physician, using ultrasound, identifies the patient 14's sartorius muscle approximately ⅓ of the distance between the patient 14's inguinal ligament and patella. The patient 14's femoral artery can be observed under the roof of the adductor canal (the sartorius muscle), and the saphenous nerve lateral to the artery. The physician then guides the needle 30/sheath 12 to the base of the sartorius muscle and injects a small amount (a few milliliters) of local anesthetic. This serves to identify the bottom of the sartorius fascia. Then the physician slightly advances the needle 30/sheath 12 through this fascia and injects more local anesthetic (about 30 milliliters or so) under the sartorius muscle (roof of adductor canal) lateral to the femoral artery. After 30 ml of local anesthetic is administered, the physician removes the needle 30, leaving the sheath 12 in the patient 14's adductor canal. A catheter 44 such as, for example, the previously described I-flow catheter, is then inserted through the sheath 12, the sheath 12 is removed, and a sterile dressing is placed over the catheter 44 where the catheter 44 exits the patient 14's skin. The proximal end 50 of the catheter 44 is connected 48 to an infusion pump 52, and administration of local anesthetic via the infusion pump 52 is commenced.

Thus, local anesthetic can be administered easily using a needle and a flexible sheath. A catheter is easily placed in a sheath. This permits easy ultrasound visualization. This also admits of a sheath made from, for example, a clear plastic polymer that is barium coated or otherwise treated to make it ultrasound opaque or semi-opaque. This would have generally the same ultrasound properties as the flexible sheath while permitting the sheath to be made somewhat stiffer. An epidural needle is again the introducer. It is also possible to make the sheath and introducer out of plastic polymers. Finally, it is possible to make the introducer/sheath a one piece, ultrasound echogenic combination, for example, out of ultrasound opaque or semi-opaque plastic polymers.

What is claimed is:

1. A method for administering an adductor canal block (ACB) to a patient, the method comprising:
   identifying the patient's sartorius muscle,
   advancing a sheath and a needle sheathed within the sheath having an open distal end through which a distal end of the needle projects to the base of the sartorius muscle,
   injecting a first amount of a local anesthetic into the sartorius muscle, wherein the first amount of the local anesthetic is injected at the base of the satorius muscle,
   identifying the bottom of the sartorius fascia,
   advancing the sheath and the sheathed needle through the sartorius fascia,
   administering a second amount of a local anesthetic under the sartorius muscle,
   removing the needle, leaving the sheath in the patient's adductor canal,
   inserting a catheter into the sheath and advancing a distal end of the catheter through the sheath to the adductor canal,
   removing the sheath while leaving the catheter in place,
   connecting a proximal end of the catheter to a source of local anesthetic, and
   commencing anesthesia, wherein a third amount of local anesthetic is delivered into the patient's adductor canal.

2. The method of claim 1 wherein identifying the patient's sartorius muscle comprises identifying the patient's sartorius muscle using ultrasound.

3. The method of claim 1 wherein connecting the proximal end of the catheter to the source of local anesthetic, and commencing anesthesia comprises connecting the proximal end of the catheter to a constant infusion pump to deliver the local anesthetic postoperatively.

4. The method of claim 1, wherein the catheter is a multi-orifice catheter and anesthesia is delivered locally from the catheter while the catheter is left in place.

* * * * *